US008898047B2

(12) United States Patent
Roymans et al.

(10) Patent No.: US 8,898,047 B2
(45) Date of Patent: Nov. 25, 2014

(54) METHODS FOR IDENTIFYING INHIBITORS AGAINST VIRUSES THAT USE A CLASS I FUSION PROTEIN

(75) Inventors: Dirk André Emmy Roymans, Mechelen (BE); Hendrik Leon Augusta Jozef De Bondt, Mechelen (BE); Eric Pierre Alexandre Arnoult, Le Vaudreuil (FR); Herman Van Vlijmen, Mechelen (BE); Jean-François Bonfanti, Andé (FR)

(73) Assignee: Janssen Pharmaceuticals NV (BE)

( * ) Notice: Subject to any disclaimer, the term of this patent is extended or adjusted under 35 U.S.C. 154(b) by 241 days.

(21) Appl. No.: 12/919,383

(22) PCT Filed: Feb. 26, 2009

(86) PCT No.: PCT/EP2009/052307
§ 371 (c)(1),
(2), (4) Date: Aug. 25, 2010

(87) PCT Pub. No.: WO2009/106580
PCT Pub. Date: Sep. 3, 2009

(65) Prior Publication Data
US 2011/0009408 A1 Jan. 13, 2011

(30) Foreign Application Priority Data

Feb. 29, 2008 (EP) ..................................... 08152183

(51) Int. Cl.
*G01N 33/566* (2006.01)
*G01N 33/00* (2006.01)
*C07K 14/135* (2006.01)

(52) U.S. Cl.
USPC ............. 703/11; 702/19; 514/235.8; 530/409

(58) Field of Classification Search
None
See application file for complete search history.

(56) References Cited

U.S. PATENT DOCUMENTS

2002/0094521 A1  7/2002  Wild et al.

OTHER PUBLICATIONS

PCT International Search Report—PCT/EP2009/052307, dated Apr. 2007.
Cianci, C., et al., "Targeting a binding pocket within the trimer-of-hairpins: Small-molecule inhibition of viral fusion", PNAS, 2004, pp. 15046-15051, vol. 101, No. 42.
Cianci, C., et al., "Filling the hole: evidence of a small molecule binding to the fusion core pocket in human respiratory syncytial virus", 2005, pp. 195-197, vol. 14(2).
Meanwell, N., et al., "Respiratory syncytial virus—the discovery and optimization of orally bioavailable fusion inhibitors", 2007, pp. 441-455, vol. 32(5).
Zhao, X., et al., "Structural characterization of the human respiratory syncytial virus fusion protein core", 2000, pp. 14172-14177, vol. 97, No. 26.
French, et al., "On the Treatment of Negative Intensity Observations", Acta Cryst. 1978, A34, pp. 517-525.
Mossessova, et al., "Ulp1-SUMO Crystal Structure and genetic analysis reveal conserved Interactions and a regulatory element essential for Cell growth in Yeast", Molecular Cell, 2000, vol. 5, pp. 865-876.
Otwinowski, et al., "Processing of X-Ray Diffraction Data Collected in Oscillation Mode", Methods in Enzymology, 1997, pp. 307-326.
Read, " Improved Fourier Coefficients for Maps Using Phases From Partial Structures with Errors", Acta Cryst., 1986, pp. 140-140.
Potterton, et al., "A Graphical User Interface to the CCP4 Program Suite", Acta Cryst., 2003, pp. 1131-1137.
Lovell et al, "The Penultimate Rotamer Library", 2000, vol. 40, pp. 389-408.
Russel, et al., "A Dual-Function Paramyxovirus F Protein Regulatory Switch Segment: Activation and Membrane Fusion", The Journal of cell Biology, 2003, pp. 363-374.
Douglas, et al., "Small Molecules VP-14637 and JNJ-2408068 Inhibit Respiratory Syncytial Virus Fusion by similar Mechanisms", Antimicrob Agents Chemother, 2005, vol. 49, No. 6, pp. 2460-2466.
Zhao, et al., "Structural Characterization of the Human Respiratory Syncytial Virus Fusion Protein Core", Proc. Natl Acad Sci USA, 2000, vol. 97, pp. 14172-14177.
Bonfanti, et al, Selection of a Respiratory syncytial Virus Fusion Inhibitor Clinical Candidate, Part 1: Improving the Pharmacokinetic Profile Using the Structure—Property Relationship .J. Med. Chem., 2007, 50, 4572-4584.
Emsley, et al., "Coot: Model-Building tools for Molecular Graphics", Acta Crystallographica Section D, 2004, pp. 2126-2132.

*Primary Examiner* — Michael Borin
(74) *Attorney, Agent, or Firm* — Mary A. Appollina

(57) ABSTRACT

The invention concerns the generation of a three dimensional model of the six helix bundle (6HB) complexed with an inhibitor and the use of that model to identify, screen and/or develop inhibitors against viruses that use a class I fusion protein. Such inhibitors of viruses that use a class I fusion protein may be effective for treating, for example, respiratory infections by Respiratory Syncytial Virus (RSV).

8 Claims, 23 Drawing Sheets

Figure 1A

Figure 1. Atomic structure coordinates for the alpha-helical coiled coil protein in complex with Compound Z comprising among others amino acids Tyr-198, Asp-200, Asp-486, Glu-487 and Phe-488 (referred to as 6HB) as derived by X-ray diffraction from crystals of that complex

```
CRYST1  63.248  63.248  63.248  90.00  90.00  90.00 P 21 3
SCALE1   0.015811  0.000000  0.000000    0.00000
SCALE2   0.000000  0.015811  0.000000    0.00000
SCALE3   0.000000  0.000000  0.015811    0.00000
```

| | | Atom type | Residue | nr | X | Y | Z | Occ | B | |
|---|---|---|---|---|---|---|---|---|---|---|
| ATOM | 1 | N | HIS | A 159 | -4.828 | 29.207 | -41.159 | 1.00 | 54.14 | N |
| ATOM | 2 | CA | HIS | A 159 | -3.532 | 28.459 | -41.095 | 1.00 | 53.78 | C |
| ATOM | 4 | CB | HIS | A 159 | -2.569 | 28.925 | -42.191 | 1.00 | 53.75 | C |
| ATOM | 12 | C | HIS | A 159 | -2.870 | 28.623 | -39.730 | 1.00 | 53.66 | C |
| ATOM | 13 | O | HIS | A 159 | -2.390 | 27.637 | -39.149 | 1.00 | 53.90 | O |
| ATOM | 17 | N | LEU | A 160 | -2.859 | 29.858 | -39.224 | 1.00 | 53.14 | N |
| ATOM | 18 | CA | LEU | A 160 | -2.134 | 30.196 | -37.991 | 1.00 | 52.68 | C |
| ATOM | 20 | CB | LEU | A 160 | -2.173 | 31.701 | -37.712 | 1.00 | 52.93 | C |
| ATOM | 23 | CG | LEU | A 160 | -1.339 | 32.152 | -36.507 | 1.00 | 53.57 | C |
| ATOM | 25 | CD1 | LEU | A 160 | -1.616 | 33.601 | -36.176 | 1.00 | 54.76 | C |
| ATOM | 29 | CD2 | LEU | A 160 | 0.151 | 31.929 | -36.755 | 1.00 | 53.96 | C |
| ATOM | 33 | C | LEU | A 160 | -2.616 | 29.458 | -36.749 | 1.00 | 52.22 | C |
| ATOM | 34 | O | LEU | A 160 | -1.798 | 29.095 | -35.911 | 1.00 | 52.12 | O |
| ATOM | 36 | N | GLU | A 161 | -3.924 | 29.253 | -36.612 | 1.00 | 51.32 | N |
| ATOM | 37 | CA | GLU | A 161 | -4.437 | 28.438 | -35.513 | 1.00 | 50.42 | C |
| ATOM | 39 | CB | GLU | A 161 | -5.972 | 28.441 | -35.445 | 1.00 | 50.98 | C |
| ATOM | 42 | CG | GLU | A 161 | -6.535 | 27.411 | -34.416 | 1.00 | 52.04 | C |
| ATOM | 45 | CD | GLU | A 161 | -7.813 | 27.859 | -33.719 | 1.00 | 52.46 | C |
| ATOM | 46 | OE1 | GLU | A 161 | -8.633 | 28.557 | -34.362 | 1.00 | 55.01 | O |
| ATOM | 47 | OE2 | GLU | A 161 | -7.997 | 27.503 | -32.528 | 1.00 | 53.59 | O |
| ATOM | 48 | C | GLU | A 161 | -3.910 | 27.014 | -35.635 | 1.00 | 49.05 | C |
| ATOM | 49 | O | GLU | A 161 | -3.707 | 26.347 | -34.625 | 1.00 | 48.74 | O |
| ATOM | 51 | N | GLY | A 162 | -3.684 | 26.555 | -36.865 | 1.00 | 47.03 | N |
| ATOM | 52 | CA | GLY | A 162 | -3.066 | 25.260 | -37.096 | 1.00 | 46.02 | C |

Figure 1B

| ATOM | 55 | C | GLY A 162 | -1.684 | 25.231 | -36.472 | 1.00 | 44.86 | C |
| ATOM | 56 | O | GLY A 162 | -1.324 | 24.269 | -35.781 | 1.00 | 43.99 | O |
| ATOM | 58 | N | GLU A 163 | -0.925 | 26.301 | -36.696 | 1.00 | 43.51 | N |
| ATOM | 59 | CA | GLU A 163 | 0.426 | 26.439 | -36.139 | 1.00 | 42.84 | C |
| ATOM | 61 | CB | GLU A 163 | 1.130 | 27.704 | -36.658 | 1.00 | 43.10 | C |
| ATOM | 64 | CG | GLU A 163 | 1.253 | 27.782 | -38.175 | 1.00 | 45.09 | C |
| ATOM | 67 | CD | GLU A 163 | 1.548 | 26.428 | -38.819 | 1.00 | 47.77 | C |
| ATOM | 68 | OE1 | GLU A 163 | 0.616 | 25.814 | -39.388 | 1.00 | 49.92 | O |
| ATOM | 69 | OE2 | GLU A 163 | 2.711 | 25.970 | -38.745 | 1.00 | 50.50 | O |
| ATOM | 70 | C | GLU A 163 | 0.389 | 26.459 | -34.619 | 1.00 | 41.47 | C |
| ATOM | 71 | O | GLU A 163 | 1.113 | 25.713 | -33.956 | 1.00 | 40.93 | O |
| ATOM | 73 | N | VAL A 164 | -0.479 | 27.289 | -34.071 | 1.00 | 39.48 | N |
| ATOM | 74 | CA | VAL A 164 | -0.643 | 27.363 | -32.633 | 1.00 | 38.61 | C |
| ATOM | 76 | CB | VAL A 164 | -1.714 | 28.400 | -32.249 | 1.00 | 39.03 | C |
| ATOM | 78 | CG1 | VAL A 164 | -2.094 | 28.294 | -30.778 | 1.00 | 39.12 | C |
| ATOM | 82 | CG2 | VAL A 164 | -1.198 | 29.803 | -32.581 | 1.00 | 39.17 | C |
| ATOM | 86 | C | VAL A 164 | -0.956 | 25.974 | -32.072 | 1.00 | 37.28 | C |
| ATOM | 87 | O | VAL A 164 | -0.425 | 25.569 | -31.022 | 1.00 | 35.08 | O |
| ATOM | 89 | N | ASN A 165 | -1.764 | 25.219 | -32.790 | 1.00 | 35.85 | N |
| ATOM | 90 | CA | ASN A 165 | -2.113 | 23.878 | -32.356 | 1.00 | 35.38 | C |
| ATOM | 92 | CB | ASN A 165 | -3.279 | 23.298 | -33.169 | 1.00 | 35.91 | C |
| ATOM | 95 | CG | ASN A 165 | -4.342 | 22.732 | -32.277 | 1.00 | 38.36 | C |
| ATOM | 96 | OD1 | ASN A 165 | -4.533 | 21.512 | -32.201 | 1.00 | 44.79 | O |
| ATOM | 97 | ND2 | ASN A 165 | -5.028 | 23.623 | -31.541 | 1.00 | 43.96 | N |
| ATOM | 100 | C | ASN A 165 | -0.935 | 22.900 | -32.372 | 1.00 | 33.85 | C |
| ATOM | 101 | O | ASN A 165 | -0.843 | 22.031 | -31.487 | 1.00 | 32.46 | O |
| ATOM | 103 | N | LYS A 166 | -0.059 | 23.027 | -33.370 | 1.00 | 31.82 | N |
| ATOM | 104 | CA | LYS A 166 | 1.157 | 22.197 | -33.460 | 1.00 | 31.37 | C |
| ATOM | 106 | CB | LYS A 166 | 1.983 | 22.463 | -34.725 | 1.00 | 32.14 | C |
| ATOM | 109 | CG | LYS A 166 | 1.450 | 21.819 | -35.979 | 1.00 | 35.93 | C |
| ATOM | 112 | CD | LYS A 166 | 2.330 | 22.168 | -37.192 | 1.00 | 35.59 | C |
| ATOM | 115 | CE | LYS A 166 | 1.501 | 22.183 | -38.485 | 1.00 | 37.81 | C |
| ATOM | 118 | NZ | LYS A 166 | 2.289 | 22.583 | -39.677 | 1.00 | 39.82 | N |
| ATOM | 122 | C | LYS A 166 | 2.026 | 22.491 | -32.241 | 1.00 | 28.53 | C |
| ATOM | 123 | O | LYS A 166 | 2.569 | 21.576 | -31.632 | 1.00 | 26.32 | O |
| ATOM | 125 | N | ILE A 167 | 2.133 | 23.753 | -31.873 | 1.00 | 26.02 | N |
| ATOM | 126 | CA | ILE A 167 | 2.940 | 24.142 | -30.697 | 1.00 | 25.40 | C |
| ATOM | 128 | CB | ILE A 167 | 3.139 | 25.669 | -30.592 | 1.00 | 25.57 | C |

Figure 1C

| | | | | | | | | |
|---|---|---|---|---|---|---|---|---|
| ATOM | 130 | CG1 | ILE A 167 | 4.009 | 26.155 | -31.754 | 1.00 25.47 | C |
| ATOM | 133 | CD1 | ILE A 167 | 4.031 | 27.700 | -31.949 | 1.00 26.81 | C |
| ATOM | 137 | CG2 | ILE A 167 | 3.808 | 26.035 | -29.268 | 1.00 25.53 | C |
| ATOM | 141 | C | ILE A 167 | 2.340 | 23.592 | -29.403 | 1.00 24.41 | C |
| ATOM | 142 | O | ILE A 167 | 3.084 | 23.115 | -28.533 | 1.00 20.19 | O |
| ATOM | 144 | N | LYS A 168 | 1.024 | 23.611 | -29.250 | 1.00 23.02 | N |
| ATOM | 145 | CA | LYS A 168 | 0.367 | 23.040 | -28.066 | 1.00 22.48 | C |
| ATOM | 147 | CB | LYS A 168 | -1.180 | 23.244 | -28.062 | 1.00 23.17 | C |
| ATOM | 150 | CG | LYS A 168 | -1.953 | 22.338 | -27.129 | 1.00 25.81 | C |
| ATOM | 153 | CD | LYS A 168 | -3.461 | 22.649 | -27.150 | 1.00 26.81 | C |
| ATOM | 156 | CE | LYS A 168 | -4.270 | 21.542 | -26.524 | 1.00 29.55 | C |
| ATOM | 159 | NZ | LYS A 168 | -5.710 | 21.882 | -26.188 | 1.00 32.70 | N |
| ATOM | 163 | C | LYS A 168 | 0.698 | 21.565 | -27.996 | 1.00 21.31 | C |
| ATOM | 164 | O | LYS A 168 | 1.093 | 21.061 | -26.958 | 1.00 18.68 | O |
| ATOM | 166 | N | SER A 169 | 0.559 | 20.855 | -29.098 | 1.00 20.54 | N |
| ATOM | 167 | CA | SER A 169 | 0.877 | 19.431 | -29.156 | 1.00 20.52 | C |
| ATOM | 169 | CB | SER A 169 | 0.555 | 18.835 | -30.531 | 1.00 22.17 | C |
| ATOM | 172 | OG | SER A 169 | -0.844 | 18.790 | -30.729 | 1.00 27.76 | O |
| ATOM | 174 | C | SER A 169 | 2.340 | 19.172 | -28.840 | 1.00 18.95 | C |
| ATOM | 175 | O | SER A 169 | 2.651 | 18.224 | -28.108 | 1.00 18.93 | O |
| ATOM | 177 | N | ALA A 170 | 3.219 | 19.994 | -29.375 | 1.00 18.05 | N |
| ATOM | 178 | CA | ALA A 170 | 4.639 | 19.862 | -29.123 | 1.00 16.72 | C |
| ATOM | 180 | CB | ALA A 170 | 5.453 | 20.867 | -29.928 | 1.00 16.98 | C |
| ATOM | 184 | C | ALA A 170 | 4.918 | 20.016 | -27.614 | 1.00 16.55 | C |
| ATOM | 185 | O | ALA A 170 | 5.694 | 19.229 | -27.035 | 1.00 15.87 | O |
| ATOM | 187 | N | LEU A 171 | 4.348 | 21.029 | -26.994 | 1.00 16.02 | N |
| ATOM | 188 | CA | LEU A 171 | 4.593 | 21.280 | -25.573 | 1.00 16.24 | C |
| ATOM | 190 | CB | LEU A 171 | 4.071 | 22.650 | -25.150 | 1.00 15.98 | C |
| ATOM | 193 | CG | LEU A 171 | 4.393 | 23.084 | -23.699 | 1.00 16.25 | C |
| ATOM | 195 | CD1 | LEU A 171 | 5.859 | 22.890 | -23.342 | 1.00 17.50 | C |
| ATOM | 199 | CD2 | LEU A 171 | 3.980 | 24.490 | -23.458 | 1.00 18.28 | C |
| ATOM | 203 | C | LEU A 171 | 4.003 | 20.163 | -24.734 | 1.00 16.04 | C |
| ATOM | 204 | O | LEU A 171 | 4.617 | 19.729 | -23.748 | 1.00 15.03 | O |
| ATOM | 206 | N | LEU A 172 | 2.849 | 19.601 | -25.092 | 1.00 16.18 | N |
| ATOM | 207 | CA | LEU A 172 | 2.339 | 18.444 | -24.403 | 1.00 16.64 | C |
| ATOM | 209 | CB | LEU A 172 | 0.953 | 18.023 | -24.921 | 1.00 18.19 | C |
| ATOM | 212 | CG | LEU A 172 | -0.176 | 18.985 | -24.579 | 1.00 20.83 | C |
| ATOM | 214 | CD1 | LEU A 172 | -1.434 | 18.732 | -25.448 | 1.00 22.70 | C |

Figure 1D

| | | | | | | | | |
|---|---|---|---|---|---|---|---|---|
| ATOM | 218 | CD2 | LEU A 172 | -0.527 | 18.900 | -23.104 | 1.00 23.71 | C |
| ATOM | 222 | C | LEU A 172 | 3.337 | 17.278 | -24.471 | 1.00 16.23 | C |
| ATOM | 223 | O | LEU A 172 | 3.526 | 16.564 | -23.458 | 1.00 15.92 | O |
| ATOM | 225 | N | SER A 173 | 4.003 | 17.079 | -25.604 | 1.00 14.92 | N |
| ATOM | 226 | CA | SER A 173 | 5.005 | 16.025 | -25.740 | 1.00 15.22 | C |
| ATOM | 228 | CB | SER A 173 | 5.368 | 15.818 | -27.214 | 0.82 15.09 | C |
| ATOM | 231 | OG | SER A 173 | 6.046 | 14.608 | -27.410 | 0.82 17.69 | O |
| ATOM | 233 | C | SER A 173 | 6.244 | 16.351 | -24.871 | 1.00 14.28 | C |
| ATOM | 234 | O | SER A 173 | 6.736 | 15.482 | -24.159 | 1.00 14.31 | O |
| ATOM | 236 | N | THR A 174 | 6.738 | 17.588 | -24.907 | 1.00 13.75 | N |
| ATOM | 237 | CA | THR A 174 | 7.844 | 18.035 | -24.042 | 1.00 14.31 | C |
| ATOM | 239 | CB | THR A 174 | 8.166 | 19.481 | -24.318 | 1.00 13.88 | C |
| ATOM | 241 | OG1 | THR A 174 | 8.553 | 19.603 | -25.693 | 1.00 14.85 | O |
| ATOM | 243 | CG2 | THR A 174 | 9.240 | 20.023 | -23.394 | 1.00 14.57 | C |
| ATOM | 247 | C | THR A 174 | 7.507 | 17.796 | -22.569 | 1.00 14.20 | C |
| ATOM | 248 | O | THR A 174 | 8.370 | 17.305 | -21.817 | 1.00 13.41 | O |
| ATOM | 250 | N | ASN A 175 | 6.291 | 18.042 | -22.172 | 1.00 13.34 | N |
| ATOM | 251 | CA | ASN A 175 | 5.889 | 17.831 | -20.807 | 1.00 14.03 | C |
| ATOM | 253 | CB | ASN A 175 | 4.492 | 18.389 | -20.541 | 1.00 13.72 | C |
| ATOM | 256 | CG | ASN A 175 | 4.463 | 19.884 | -20.440 | 1.00 15.57 | C |
| ATOM | 257 | OD1 | ASN A 175 | 5.512 | 20.527 | -20.438 | 1.00 14.89 | O |
| ATOM | 258 | ND2 | ASN A 175 | 3.236 | 20.481 | -20.313 | 1.00 15.37 | N |
| ATOM | 261 | C | ASN A 175 | 5.958 | 16.346 | -20.438 | 1.00 14.04 | C |
| ATOM | 262 | O | ASN A 175 | 6.463 | 15.980 | -19.356 | 1.00 14.07 | O |
| ATOM | 264 | N | LYS A 176 | 5.527 | 15.469 | -21.301 | 1.00 14.09 | N |
| ATOM | 265 | CA | LYS A 176 | 5.673 | 14.027 | -21.108 | 1.00 15.39 | C |
| ATOM | 267 | CB | LYS A 176 | 4.985 | 13.226 | -22.192 | 1.00 16.29 | C |
| ATOM | 270 | CG | LYS A 176 | 3.497 | 13.380 | -22.138 | 1.00 20.86 | C |
| ATOM | 273 | CD | LYS A 176 | 2.794 | 12.656 | -23.270 | 1.00 23.78 | C |
| ATOM | 276 | CE | LYS A 176 | 1.279 | 12.953 | -23.278 | 1.00 28.81 | C |
| ATOM | 279 | NZ | LYS A 176 | 0.682 | 12.790 | -24.656 | 1.00 32.35 | N |
| ATOM | 283 | C | LYS A 176 | 7.125 | 13.632 | -21.013 | 1.00 13.82 | C |
| ATOM | 284 | O | LYS A 176 | 7.472 | 12.735 | -20.201 | 1.00 14.04 | O |
| ATOM | 286 | N | ALA A 177 | 8.003 | 14.271 | -21.774 | 1.00 12.57 | N |
| ATOM | 287 | CA | ALA A 177 | 9.455 | 14.035 | -21.629 | 1.00 13.83 | C |
| ATOM | 289 | CB | ALA A 177 | 10.238 | 14.834 | -22.657 | 1.00 14.15 | C |
| ATOM | 293 | C | ALA A 177 | 9.956 | 14.350 | -20.217 | 1.00 13.48 | C |
| ATOM | 294 | O | ALA A 177 | 10.737 | 13.602 | -19.620 | 1.00 13.76 | O |

Figure 1E

| ATOM | 296 | N   | VAL A 178  | 9.504  | 15.451 | -19.682 | 1.00 | 12.55 | N |
| ---- | --- | --- | ---------- | ------ | ------ | ------- | ---- | ----- | - |
| ATOM | 297 | CA  | VAL A 178  | 9.989  | 15.874 | -18.372 | 1.00 | 13.39 | C |
| ATOM | 299 | CB  | VAL A 178  | 9.613  | 17.339 | -18.066 | 1.00 | 13.95 | C |
| ATOM | 301 | CG1 | VAL A 178  | 10.034 | 17.682 | -16.606 | 1.00 | 14.05 | C |
| ATOM | 305 | CG2 | VAL A 178  | 10.268 | 18.269 | -19.060 | 1.00 | 13.22 | C |
| ATOM | 309 | C   | VAL A 178  | 9.437  | 14.940 | -17.303 | 1.00 | 12.99 | C |
| ATOM | 310 | O   | VAL A 178  | 10.146 | 14.575 | -16.357 | 1.00 | 13.00 | O |
| ATOM | 312 | N   | VAL A 179  | 8.185  | 14.502 | -17.416 | 1.00 | 13.16 | N |
| ATOM | 313 | CA  | VAL A 179  | 7.637  | 13.506 | -16.489 | 1.00 | 14.00 | C |
| ATOM | 315 | CB  | VAL A 179  | 6.144  | 13.254 | -16.760 | 1.00 | 13.74 | C |
| ATOM | 317 | CG1 | VAL A 179  | 5.648  | 12.129 | -15.885 | 1.00 | 16.76 | C |
| ATOM | 321 | CG2 | VAL A 179  | 5.341  | 14.519 | -16.554 | 1.00 | 16.12 | C |
| ATOM | 325 | C   | VAL A 179  | 8.430  | 12.207 | -16.536 | 1.00 | 13.53 | C |
| ATOM | 326 | O   | VAL A 179  | 8.802  | 11.637 | -15.496 | 1.00 | 14.76 | O |
| ATOM | 328 | N   | SER A 180  | 8.721  | 11.702 | -17.744 | 1.00 | 13.68 | N |
| ATOM | 329 | CA  | ASER A 180 | 9.480  | 10.486 | -17.893 | 0.75 | 14.69 | C |
| ATOM | 330 | CA  | BSER A 180 | 9.489  | 10.496 | -17.906 | 0.25 | 13.99 | C |
| ATOM | 333 | CB  | ASER A 180 | 9.663  | 10.098 | -19.372 | 0.75 | 15.08 | C |
| ATOM | 334 | CB  | BSER A 180 | 9.690  | 10.231 | -19.389 | 0.25 | 14.15 | C |
| ATOM | 339 | OG  | ASER A 180 | 8.415  | 9.898  | -20.048 | 0.75 | 16.47 | O |
| ATOM | 340 | OG  | BSER A 180 | 10.308 | 8.984  | -19.567 | 0.25 | 14.49 | O |
| ATOM | 343 | C   | SER A 180  | 10.853 | 10.603 | -17.232 | 1.00 | 13.61 | C |
| ATOM | 344 | O   | SER A 180  | 11.286 | 9.732  | -16.487 | 1.00 | 13.65 | O |
| ATOM | 346 | N   | LEU A 181  | 11.550 | 11.695 | -17.511 | 1.00 | 13.18 | N |
| ATOM | 347 | CA  | LEU A 181  | 12.881 | 11.904 | -16.934 | 1.00 | 13.26 | C |
| ATOM | 349 | CB  | LEU A 181  | 13.569 | 13.106 | -17.550 | 1.00 | 12.21 | C |
| ATOM | 352 | CG  | LEU A 181  | 15.046 | 13.245 | -17.169 | 1.00 | 14.03 | C |
| ATOM | 354 | CD1 | LEU A 181  | 15.846 | 12.090 | -17.627 | 1.00 | 14.89 | C |
| ATOM | 358 | CD2 | LEU A 181  | 15.619 | 14.524 | -17.728 | 1.00 | 14.63 | C |
| ATOM | 362 | C   | LEU A 181  | 12.781 | 12.019 | -15.412 | 1.00 | 12.62 | C |
| ATOM | 363 | O   | LEU A 181  | 13.641 | 11.477 | -14.717 | 1.00 | 13.07 | O |
| ATOM | 365 | N   | SER A 182  | 11.786 | 12.717 | -14.913 | 1.00 | 13.14 | N |
| ATOM | 366 | CA  | SER A 182  | 11.585 | 12.851 | -13.452 | 1.00 | 13.53 | C |
| ATOM | 368 | CB  | SER A 182  | 10.384 | 13.740 | -13.159 | 1.00 | 14.27 | C |
| ATOM | 371 | OG  | SER A 182  | 10.489 | 15.082 | -13.593 | 1.00 | 16.80 | O |
| ATOM | 373 | C   | SER A 182  | 11.387 | 11.493 | -12.834 | 1.00 | 13.81 | C |
| ATOM | 374 | O   | SER A 182  | 11.950 | 11.210 | -11.752 | 1.00 | 13.92 | O |
| ATOM | 376 | N   | ASN A 183  | 10.610 | 10.626 | -13.482 | 1.00 | 14.22 | N |

Figure 1F

| | | | | | | | | | |
|---|---|---|---|---|---|---|---|---|---|
| ATOM | 377 | CA | ASN A 183 | 10.417 | 9.285 | -12.943 | 1.00 | 15.88 | C |
| ATOM | 379 | CB | ASN A 183 | 9.284 | 8.557 | -13.695 | 1.00 | 18.70 | C |
| ATOM | 382 | CG | ASN A 183 | 7.911 | 9.183 | -13.424 | 1.00 | 22.40 | C |
| ATOM | 383 | OD1 | ASN A 183 | 7.697 | 9.898 | -12.426 | 1.00 | 31.70 | O |
| ATOM | 384 | ND2 | ASN A 183 | 6.970 | 8.958 | -14.352 | 1.00 | 25.69 | N |
| ATOM | 387 | C | ASN A 183 | 11.719 | 8.478 | -12.945 | 1.00 | 14.95 | C |
| ATOM | 388 | O | ASN A 183 | 12.041 | 7.768 | -11.969 | 1.00 | 15.69 | O |
| ATOM | 390 | N | GLY A 184 | 12.538 | 8.587 | -13.994 | 1.00 | 14.48 | N |
| ATOM | 391 | CA | GLY A 184 | 13.832 | 7.941 | -14.006 | 1.00 | 13.91 | C |
| ATOM | 394 | C | GLY A 184 | 14.760 | 8.442 | -12.887 | 1.00 | 13.69 | C |
| ATOM | 395 | O | GLY A 184 | 15.437 | 7.673 | -12.220 | 1.00 | 14.08 | O |
| ATOM | 397 | N | VAL A 185 | 14.816 | 9.767 | -12.688 | 1.00 | 12.76 | N |
| ATOM | 398 | CA | VAL A 185 | 15.608 | 10.336 | -11.577 | 1.00 | 13.10 | C |
| ATOM | 400 | CB | VAL A 185 | 15.638 | 11.846 | -11.652 | 1.00 | 12.53 | C |
| ATOM | 402 | CG1 | VAL A 185 | 16.414 | 12.458 | -10.480 | 1.00 | 13.70 | C |
| ATOM | 406 | CG2 | VAL A 185 | 16.330 | 12.308 | -12.958 | 1.00 | 13.88 | C |
| ATOM | 410 | C | VAL A 185 | 15.071 | 9.844 | -10.218 | 1.00 | 12.61 | C |
| ATOM | 411 | O | VAL A 185 | 15.888 | 9.542 | -9.338 | 1.00 | 12.43 | O |
| ATOM | 413 | N | SER A 186 | 13.765 | 9.679 | -10.052 | 1.00 | 13.28 | N |
| ATOM | 414 | CA A | SER A 186 | 13.230 | 9.173 | -8.795 | 0.75 | 13.48 | C |
| ATOM | 415 | CA B | SER A 186 | 13.174 | 9.134 | -8.818 | 0.25 | 13.42 | C |
| ATOM | 418 | CB A | SER A 186 | 11.722 | 9.269 | -8.820 | 0.75 | 13.85 | C |
| ATOM | 419 | CB B | SER A 186 | 11.651 | 9.041 | -8.960 | 0.25 | 13.74 | C |
| ATOM | 424 | OG A | SER A 186 | 11.199 | 8.687 | -7.641 | 0.75 | 16.01 | O |
| ATOM | 425 | OG B | SER A 186 | 11.034 | 10.313 | -9.001 | 0.25 | 14.95 | O |
| ATOM | 428 | C | SER A 186 | 13.732 | 7.738 | -8.532 | 1.00 | 13.42 | C |
| ATOM | 429 | O | SER A 186 | 14.188 | 7.408 | -7.444 | 1.00 | 13.81 | O |
| ATOM | 431 | N | VAL A 187 | 13.713 | 6.873 | -9.534 | 1.00 | 12.82 | N |
| ATOM | 432 | CA | VAL A 187 | 14.216 | 5.520 | -9.384 | 1.00 | 13.57 | C |
| ATOM | 434 | CB | VAL A 187 | 13.948 | 4.674 | -10.653 | 1.00 | 14.52 | C |
| ATOM | 436 | CG1 | VAL A 187 | 14.566 | 3.314 | -10.564 | 1.00 | 16.79 | C |
| ATOM | 440 | CG2 | VAL A 187 | 12.451 | 4.504 | -10.851 | 1.00 | 15.56 | C |
| ATOM | 444 | C | VAL A 187 | 15.697 | 5.557 | -9.081 | 1.00 | 12.92 | C |
| ATOM | 445 | O | VAL A 187 | 16.194 | 4.826 | -8.203 | 1.00 | 12.94 | O |
| ATOM | 447 | N | LEU A 188 | 16.451 | 6.360 | -9.807 | 1.00 | 12.14 | N |
| ATOM | 448 | CA | LEU A 188 | 17.888 | 6.445 | -9.570 | 1.00 | 12.82 | C |
| ATOM | 450 | CB | LEU A 188 | 18.592 | 7.353 | -10.588 | 1.00 | 13.19 | C |
| ATOM | 453 | CG | LEU A 188 | 20.116 | 7.405 | -10.509 | 1.00 | 13.18 | C |

Figure 1G

| | | | | | | | | |
|---|---|---|---|---|---|---|---|---|
| ATOM | 455 | CD1 | LEU A 188 | 20.625 | 8.474 | -11.477 | 1.00 15.00 | C |
| ATOM | 459 | CD2 | LEU A 188 | 20.675 | 6.087 | -10.846 | 1.00 14.60 | C |
| ATOM | 463 | C | LEU A 188 | 18.169 | 6.898 | -8.123 | 1.00 12.04 | C |
| ATOM | 464 | O | LEU A 188 | 19.084 | 6.386 | -7.490 | 1.00 12.10 | O |
| ATOM | 466 | N | THR A 189 | 17.448 | 7.889 | -7.640 | 1.00 12.58 | N |
| ATOM | 467 | CA | THR A 189 | 17.614 | 8.395 | -6.296 | 1.00 12.81 | C |
| ATOM | 469 | CB | THR A 189 | 16.627 | 9.506 | -6.085 | 1.00 11.93 | C |
| ATOM | 471 | OG1 | THR A 189 | 16.892 | 10.589 | -6.975 | 1.00 13.60 | O |
| ATOM | 473 | CG2 | THR A 189 | 16.693 | 10.053 | -4.679 | 1.00 13.07 | C |
| ATOM | 477 | C | THR A 189 | 17.424 | 7.252 | -5.279 | 1.00 12.15 | C |
| ATOM | 478 | O | THR A 189 | 18.196 | 7.105 | -4.294 | 1.00 13.12 | O |
| ATOM | 480 | N | SER A 190 | 16.383 | 6.440 | -5.480 | 1.00 13.57 | N |
| ATOM | 481 | CA A | SER A 190 | 16.134 | 5.331 | -4.569 | 0.25 13.88 | C |
| ATOM | 482 | CA B | SER A 190 | 16.129 | 5.323 | -4.581 | 0.25 13.48 | C |
| ATOM | 483 | CA C | SER A 190 | 16.119 | 5.297 | -4.606 | 0.50 14.12 | C |
| ATOM | 487 | CB A | SER A 190 | 14.810 | 4.659 | -4.902 | 0.25 14.36 | C |
| ATOM | 488 | CB B | SER A 190 | 14.808 | 4.651 | -4.942 | 0.25 13.81 | C |
| ATOM | 489 | CB C | SER A 190 | 14.843 | 4.616 | -5.082 | 0.50 14.91 | C |
| ATOM | 496 | OG A | SER A 190 | 14.890 | 3.986 | -6.140 | 0.25 16.14 | O |
| ATOM | 497 | OG B | SER A 190 | 13.716 | 5.508 | -4.649 | 0.25 12.32 | O |
| ATOM | 498 | OG C | SER A 190 | 14.500 | 3.536 | -4.239 | 0.50 18.35 | O |
| ATOM | 502 | C | SER A 190 | 17.293 | 4.345 | -4.592 | 1.00 14.08 | C |
| ATOM | 503 | O | SER A 190 | 17.660 | 3.816 | -3.545 | 1.00 15.01 | O |
| ATOM | 505 | N | LYS A 191 | 17.887 | 4.089 | -5.752 | 1.00 12.87 | N |
| ATOM | 506 | CA | LYS A 191 | 19.005 | 3.169 | -5.867 | 1.00 13.88 | C |
| ATOM | 508 | CB | LYS A 191 | 19.328 | 2.766 | -7.301 | 1.00 14.82 | C |
| ATOM | 511 | CG | LYS A 191 | 18.236 | 1.957 | -8.022 | 1.00 18.74 | C |
| ATOM | 514 | CD | LYS A 191 | 17.626 | 0.795 | -7.188 | 1.00 21.14 | C |
| ATOM | 517 | CE | LYS A 191 | 16.312 | 1.137 | -6.571 | 1.00 22.77 | C |
| ATOM | 520 | NZ | LYS A 191 | 15.617 | -0.007 | -5.799 | 1.00 27.65 | N |
| ATOM | 524 | C | LYS A 191 | 20.262 | 3.735 | -5.202 | 1.00 12.86 | C |
| ATOM | 525 | O | LYS A 191 | 21.043 | 2.964 | -4.643 | 1.00 13.45 | O |
| ATOM | 527 | N | VAL A 192 | 20.495 | 5.047 | -5.256 | 1.00 12.61 | N |
| ATOM | 528 | CA | VAL A 192 | 21.636 | 5.661 | -4.557 | 1.00 13.56 | C |
| ATOM | 530 | CB | VAL A 192 | 21.806 | 7.132 | -5.015 | 1.00 12.84 | C |
| ATOM | 532 | CG1 | VAL A 192 | 22.815 | 7.871 | -4.168 | 1.00 15.22 | C |
| ATOM | 536 | CG2 | VAL A 192 | 22.234 | 7.224 | -6.483 | 1.00 14.16 | C |
| ATOM | 540 | C | VAL A 192 | 21.439 | 5.521 | -3.033 | 1.00 13.27 | C |

Figure 1H

| ATOM | 541 | O | VAL A 192 | 22.409 | 5.180 | -2.295 | 1.00 | 13.84 | O |
| ATOM | 543 | N | LEU A 193 | 20.240 | 5.767 | -2.554 | 1.00 | 13.92 | N |
| ATOM | 544 | CA | LEU A 193 | 19.967 | 5.555 | -1.132 | 1.00 | 15.08 | C |
| ATOM | 546 | CB | LEU A 193 | 18.561 | 6.053 | -0.777 | 1.00 | 14.10 | C |
| ATOM | 549 | CG | LEU A 193 | 18.175 | 5.883 | 0.724 | 1.00 | 17.14 | C |
| ATOM | 551 | CD1 | LEU A 193 | 19.107 | 6.668 | 1.600 | 1.00 | 17.80 | C |
| ATOM | 555 | CD2 | LEU A 193 | 16.738 | 6.300 | 0.940 | 1.00 | 17.80 | C |
| ATOM | 559 | C | LEU A 193 | 20.163 | 4.088 | -0.748 | 1.00 | 14.52 | C |
| ATOM | 560 | O | LEU A 193 | 20.817 | 3.793 | 0.271 | 1.00 | 14.71 | O |
| ATOM | 562 | N | ASP A 194 | 19.751 | 3.159 | -1.595 | 1.00 | 14.45 | N |
| ATOM | 563 | CA | ASP A 194 | 19.960 | 1.726 | -1.335 | 1.00 | 15.68 | C |
| ATOM | 565 | CB | ASP A 194 | 19.320 | 0.818 | -2.406 | 1.00 | 15.46 | C |
| ATOM | 568 | CG | ASP A 194 | 17.806 | 0.706 | -2.304 | 1.00 | 19.11 | C |
| ATOM | 569 | OD1 | ASP A 194 | 17.202 | 1.157 | -1.297 | 1.00 | 21.43 | O |
| ATOM | 570 | OD2 | ASP A 194 | 17.236 | 0.195 | -3.308 | 1.00 | 21.57 | O |
| ATOM | 571 | C | ASP A 194 | 21.439 | 1.403 | -1.231 | 1.00 | 15.84 | C |
| ATOM | 572 | O | ASP A 194 | 21.882 | 0.629 | -0.359 | 1.00 | 15.65 | O |
| ATOM | 574 | N | LEU A 195 | 22.252 | 1.957 | -2.112 | 1.00 | 14.27 | N |
| ATOM | 575 | CA A | LEU A 195 | 23.702 | 1.728 | -2.089 | 0.50 | 14.98 | C |
| ATOM | 576 | CA B | LEU A 195 | 23.660 | 1.692 | -2.103 | 0.50 | 15.12 | C |
| ATOM | 579 | CB A | LEU A 195 | 24.438 | 2.428 | -3.243 | 0.50 | 15.56 | C |
| ATOM | 580 | CB B | LEU A 195 | 24.266 | 2.290 | -3.370 | 0.50 | 15.64 | C |
| ATOM | 585 | CG A | LEU A 195 | 24.414 | 1.778 | -4.610 | 0.50 | 14.95 | C |
| ATOM | 586 | CG B | LEU A 195 | 25.659 | 1.838 | -3.741 | 0.50 | 15.36 | C |
| ATOM | 589 | CD1A | LEU A 195 | 25.306 | 2.579 | -5.568 | 0.50 | 15.42 | C |
| ATOM | 590 | CD1B | LEU A 195 | 25.805 | 0.316 | -3.829 | 0.50 | 17.59 | C |
| ATOM | 597 | CD2A | LEU A 195 | 24.887 | 0.320 | -4.520 | 0.50 | 13.00 | C |
| ATOM | 598 | CD2B | LEU A 195 | 26.044 | 2.460 | -5.057 | 0.50 | 15.84 | C |
| ATOM | 605 | C | LEU A 195 | 24.277 | 2.240 | -0.797 | 1.00 | 15.44 | C |
| ATOM | 606 | O | LEU A 195 | 25.140 | 1.587 | -0.166 | 1.00 | 14.76 | O |
| ATOM | 608 | N | LYS A 196 | 23.879 | 3.437 | -0.376 | 1.00 | 14.77 | N |
| ATOM | 609 | CA | LYS A 196 | 24.400 | 4.022 | 0.872 | 1.00 | 14.56 | C |
| ATOM | 611 | CB | LYS A 196 | 23.841 | 5.425 | 1.055 | 1.00 | 14.67 | C |
| ATOM | 614 | CG | LYS A 196 | 24.354 | 6.101 | 2.314 | 1.00 | 15.79 | C |
| ATOM | 617 | CD | LYS A 196 | 23.302 | 6.241 | 3.375 | 1.00 | 15.47 | C |
| ATOM | 620 | CE | LYS A 196 | 23.756 | 7.083 | 4.611 | 1.00 | 16.48 | C |
| ATOM | 623 | NZ | LYS A 196 | 22.675 | 7.390 | 5.637 | 1.00 | 17.93 | N |
| ATOM | 627 | C | LYS A 196 | 24.054 | 3.121 | 2.064 | 1.00 | 14.24 | C |

Figure 1I

| | | | | | | | | | |
|---|---|---|---|---|---|---|---|---|---|
| ATOM | 628 | O | LYS | A | 196 | 24.887 | 2.851 | 2.929 | 1.00 15.01 | O |
| ATOM | 630 | N | ASN | A | 197 | 22.809 | 2.676 | 2.130 | 1.00 13.71 | N |
| ATOM | 631 | CA | ASN | A | 197 | 22.372 | 1.773 | 3.217 | 1.00 15.68 | C |
| ATOM | 633 | CB | ASN | A | 197 | 20.857 | 1.661 | 3.188 | 1.00 15.71 | C |
| ATOM | 636 | CG | ASN | A | 197 | 20.160 | 2.877 | 3.732 | 1.00 18.43 | C |
| ATOM | 637 | OD1 | ASN | A | 197 | 20.673 | 3.569 | 4.597 | 1.00 24.40 | O |
| ATOM | 638 | ND2 | ASN | A | 197 | 18.981 | 3.128 | 3.216 | 1.00 20.37 | N |
| ATOM | 641 | C | ASN | A | 197 | 23.082 | 0.423 | 3.154 | 1.00 16.25 | C |
| ATOM | 642 | O | ASN | A | 197 | 23.454 | -0.133 | 4.182 | 1.00 16.41 | O |
| ATOM | 644 | N | TYR | A | 198 | 23.296 | -0.142 | 1.970 | 1.00 15.69 | N |
| ATOM | 645 | CA | TYR | A | 198 | 24.054 | -1.379 | 1.829 | 1.00 16.49 | C |
| ATOM | 647 | CB | TYR | A | 198 | 24.071 | -1.720 | 0.342 | 1.00 17.85 | C |
| ATOM | 650 | CG | TYR | A | 198 | 24.738 | -2.975 | -0.137 | 1.00 17.62 | C |
| ATOM | 651 | CD1 | TYR | A | 198 | 24.100 | -4.195 | -0.050 | 1.00 17.55 | C |
| ATOM | 653 | CE1 | TYR | A | 198 | 24.640 | -5.320 | -0.578 | 1.00 19.52 | C |
| ATOM | 655 | CZ | TYR | A | 198 | 25.846 | -5.252 | -1.203 | 1.00 20.17 | C |
| ATOM | 656 | OH | TYR | A | 198 | 26.385 | -6.425 | -1.730 | 1.00 22.35 | O |
| ATOM | 658 | CE2 | TYR | A | 198 | 26.535 | -4.074 | -1.295 | 1.00 21.46 | C |
| ATOM | 660 | CD2 | TYR | A | 198 | 25.972 | -2.931 | -0.763 | 1.00 20.20 | C |
| ATOM | 662 | C | TYR | A | 198 | 25.461 | -1.219 | 2.373 | 1.00 17.41 | C |
| ATOM | 663 | O | TYR | A | 198 | 25.952 | -2.076 | 3.102 | 1.00 18.27 | O |
| ATOM | 665 | N | ILE | A | 199 | 26.136 | -0.151 | 2.002 | 1.00 18.14 | N |
| ATOM | 666 | CA | ILE | A | 199 | 27.481 | 0.095 | 2.539 | 1.00 20.22 | C |
| ATOM | 668 | CB | ILE | A | 199 | 28.065 | 1.378 | 1.954 | 1.00 21.44 | C |
| ATOM | 670 | CG1 | ILE | A | 199 | 28.381 | 1.215 | 0.470 | 1.00 22.77 | C |
| ATOM | 673 | CD1 | ILE | A | 199 | 28.374 | 2.515 | -0.277 | 1.00 24.06 | C |
| ATOM | 677 | CG2 | ILE | A | 199 | 29.303 | 1.819 | 2.720 | 1.00 22.06 | C |
| ATOM | 681 | C | ILE | A | 199 | 27.457 | 0.187 | 4.069 | 1.00 20.48 | C |
| ATOM | 682 | O | ILE | A | 199 | 28.298 | -0.462 | 4.743 | 1.00 22.45 | O |
| ATOM | 684 | N | ASP | A | 200 | 26.568 | 0.987 | 4.634 | 1.00 19.09 | N |
| ATOM | 685 | CA | ASP | A | 200 | 26.579 | 1.172 | 6.082 | 1.00 20.01 | C |
| ATOM | 687 | CB | ASP | A | 200 | 25.761 | 2.373 | 6.458 | 1.00 19.00 | C |
| ATOM | 690 | CG | ASP | A | 200 | 26.499 | 3.690 | 6.290 | 1.00 19.66 | C |
| ATOM | 691 | OD1 | ASP | A | 200 | 25.889 | 4.729 | 6.551 | 1.00 21.23 | O |
| ATOM | 692 | OD2 | ASP | A | 200 | 27.706 | 3.675 | 5.938 | 1.00 20.95 | O |
| ATOM | 693 | C | ASP | A | 200 | 26.097 | -0.055 | 6.869 | 1.00 21.09 | C |
| ATOM | 694 | O | ASP | A | 200 | 26.564 | -0.326 | 8.004 | 1.00 22.15 | O |
| ATOM | 696 | N | LYS | A | 201 | 25.175 | -0.817 | 6.306 | 1.00 21.65 | N |

Figure 1J

| | | | | | | | | |
|---|---|---|---|---|---|---|---|---|
| ATOM | 697 | CA | LYS A 201 | 24.486 | -1.880 | 7.063 | 1.00 23.14 | C |
| ATOM | 699 | CB | LYS A 201 | 22.972 | -1.671 | 6.990 | 1.00 21.96 | C |
| ATOM | 702 | CG | LYS A 201 | 22.530 | -0.337 | 7.450 | 1.00 23.20 | C |
| ATOM | 705 | CD | LYS A 201 | 21.070 | -0.103 | 7.182 | 1.00 24.78 | C |
| ATOM | 708 | CE | LYS A 201 | 20.608 | 1.242 | 7.611 | 1.00 26.44 | C |
| ATOM | 711 | NZ | LYS A 201 | 19.143 | 1.394 | 7.351 | 1.00 27.59 | N |
| ATOM | 715 | C | LYS A 201 | 24.878 | -3.296 | 6.628 | 1.00 23.64 | C |
| ATOM | 716 | O | LYS A 201 | 24.642 | -4.268 | 7.383 | 1.00 25.39 | O |
| ATOM | 718 | N | GLN A 202 | 25.490 | -3.473 | 5.449 | 1.00 24.96 | N |
| ATOM | 719 | CA | GLN A 202 | 26.027 | -4.766 | 5.012 | 1.00 26.91 | C |
| ATOM | 721 | CB | GLN A 202 | 25.455 | -5.135 | 3.618 | 1.00 26.84 | C |
| ATOM | 724 | CG | GLN A 202 | 24.038 | -5.625 | 3.663 | 1.00 30.53 | C |
| ATOM | 727 | CD | GLN A 202 | 23.931 | -7.040 | 4.214 | 1.00 31.58 | C |
| ATOM | 728 | OE1 | GLN A 202 | 23.763 | -7.236 | 5.421 | 1.00 36.97 | O |
| ATOM | 729 | NE2 | GLN A 202 | 24.011 | -8.012 | 3.348 | 1.00 31.93 | N |
| ATOM | 732 | C | GLN A 202 | 27.555 | -4.834 | 4.971 | 1.00 28.27 | C |
| ATOM | 733 | O | GLN A 202 | 28.151 | -5.861 | 5.377 | 1.00 27.68 | O |
| ATOM | 735 | N | LEU A 203 | 28.194 | -3.789 | 4.456 | 1.00 29.96 | N |
| ATOM | 736 | CA | LEU A 203 | 29.641 | -3.787 | 4.251 | 1.00 30.90 | C |
| ATOM | 738 | CB | LEU A 203 | 30.039 | -2.747 | 3.209 | 1.00 32.27 | C |
| ATOM | 741 | CG | LEU A 203 | 30.253 | -3.160 | 1.771 | 1.00 35.93 | C |
| ATOM | 743 | CD1 | LEU A 203 | 31.624 | -3.818 | 1.609 | 1.00 38.74 | C |
| ATOM | 747 | CD2 | LEU A 203 | 29.134 | -4.067 | 1.318 | 1.00 39.20 | C |
| ATOM | 751 | C | LEU A 203 | 30.366 | -3.462 | 5.548 | 1.00 31.54 | C |
| ATOM | 752 | O | LEU A 203 | 31.248 | -4.221 | 5.989 | 1.00 31.26 | O |
| ATOM | 754 | N | LEU A 204 | 30.020 | -2.327 | 6.150 | 1.00 31.08 | N |
| ATOM | 755 | CA | LEU A 204 | 30.767 | -1.834 | 7.303 | 1.00 33.27 | C |
| ATOM | 757 | CB | LEU A 204 | 30.330 | -0.410 | 7.713 | 1.00 32.57 | C |
| ATOM | 760 | CG | LEU A 204 | 31.083 | 0.744 | 7.039 | 1.00 35.94 | C |
| ATOM | 762 | CD1 | LEU A 204 | 30.507 | 2.076 | 7.456 | 1.00 37.24 | C |
| ATOM | 766 | CD2 | LEU A 204 | 32.593 | 0.685 | 7.356 | 1.00 37.98 | C |
| ATOM | 770 | C | LEU A 204 | 30.716 | -2.797 | 8.491 | 1.00 33.82 | C |
| ATOM | 771 | O | LEU A 204 | 31.730 | -2.969 | 9.164 | 1.00 34.07 | O |
| ATOM | 773 | N | PRO A 205 | 29.556 | -3.424 | 8.767 | 1.00 35.10 | N |
| ATOM | 774 | CA | PRO A 205 | 29.523 | -4.389 | 9.891 | 1.00 36.70 | C |
| ATOM | 776 | CB | PRO A 205 | 28.033 | -4.737 | 10.024 | 1.00 36.75 | C |
| ATOM | 779 | CG | PRO A 205 | 27.319 | -3.573 | 9.338 | 1.00 35.81 | C |
| ATOM | 782 | CD | PRO A 205 | 28.216 | -3.223 | 8.191 | 1.00 34.99 | C |

Figure 1K

| ATOM | 785 | C | PRO A 205 | 30.372 | -5.656 | 9.750 | 1.00 | 38.17 | C |
|---|---|---|---|---|---|---|---|---|---|
| ATOM | 786 | O | PRO A 205 | 30.753 | -6.247 | 10.774 | 1.00 | 38.75 | O |
| ATOM | 787 | N | ILE A 206 | 30.669 | -6.081 | 8.528 | 1.00 | 39.58 | N |
| ATOM | 788 | CA | ILE A 206 | 31.536 | -7.239 | 8.335 | 1.00 | 40.64 | C |
| ATOM | 790 | CB | ILE A 206 | 31.032 | -8.143 | 7.195 | 1.00 | 40.77 | C |
| ATOM | 792 | CG1 | ILE A 206 | 31.249 | -7.510 | 5.815 | 1.00 | 40.87 | C |
| ATOM | 795 | CD1 | ILE A 206 | 30.676 | -8.349 | 4.664 | 1.00 | 41.32 | C |
| ATOM | 799 | CG2 | ILE A 206 | 29.548 | -8.460 | 7.407 | 1.00 | 40.14 | C |
| ATOM | 803 | C | ILE A 206 | 32.991 | -6.819 | 8.104 | 1.00 | 41.79 | C |
| ATOM | 804 | O | ILE A 206 | 33.878 | -7.670 | 8.065 | 1.00 | 42.67 | O |
| ATOM | 806 | N | ALA A 207 | 33.225 | -5.518 | 7.942 | 1.00 | 43.05 | N |
| ATOM | 807 | CA | ALA A 207 | 34.566 | -4.972 | 7.722 | 1.00 | 43.69 | C |
| ATOM | 809 | CB | ALA A 207 | 34.502 | -3.738 | 6.809 | 1.00 | 43.97 | C |
| ATOM | 813 | C | ALA A 207 | 35.174 | -4.618 | 9.073 | 1.00 | 44.67 | C |
| ATOM | 814 | O | ALA A 207 | 35.331 | -5.501 | 9.932 | 1.00 | 46.43 | O |
| ATOM | 816 | N | PHE B 483 | 24.534 | -8.417 | -16.855 | 1.00 | 34.85 | N |
| ATOM | 817 | CA | PHE B 483 | 23.541 | -7.334 | -16.575 | 1.00 | 34.08 | C |
| ATOM | 819 | CB | PHE B 483 | 24.083 | -5.961 | -16.992 | 1.00 | 33.87 | C |
| ATOM | 822 | CG | PHE B 483 | 23.130 | -4.800 | -16.751 | 1.00 | 34.37 | C |
| ATOM | 823 | CD1 | PHE B 483 | 23.215 | -4.034 | -15.606 | 1.00 | 32.39 | C |
| ATOM | 825 | CE1 | PHE B 483 | 22.370 | -2.966 | -15.406 | 1.00 | 31.80 | C |
| ATOM | 827 | CZ | PHE B 483 | 21.459 | -2.635 | -16.333 | 1.00 | 30.82 | C |
| ATOM | 829 | CE2 | PHE B 483 | 21.355 | -3.383 | -17.488 | 1.00 | 32.29 | C |
| ATOM | 831 | CD2 | PHE B 483 | 22.193 | -4.442 | -17.700 | 1.00 | 34.65 | C |
| ATOM | 833 | C | PHE B 483 | 22.280 | -7.635 | -17.340 | 1.00 | 33.65 | C |
| ATOM | 834 | O | PHE B 483 | 22.350 | -7.862 | -18.565 | 1.00 | 35.39 | O |
| ATOM | 838 | N | PRO B 484 | 21.124 | -7.614 | -16.651 | 1.00 | 32.06 | N |
| ATOM | 839 | CA | PRO B 484 | 20.942 | -7.354 | -15.216 | 1.00 | 30.64 | C |
| ATOM | 841 | CB | PRO B 484 | 19.527 | -6.815 | -15.144 | 1.00 | 30.29 | C |
| ATOM | 844 | CG | PRO B 484 | 18.841 | -7.459 | -16.315 | 1.00 | 31.07 | C |
| ATOM | 847 | CD | PRO B 484 | 19.840 | -7.805 | -17.334 | 1.00 | 32.71 | C |
| ATOM | 850 | C | PRO B 484 | 21.069 | -8.610 | -14.362 | 1.00 | 30.88 | C |
| ATOM | 851 | O | PRO B 484 | 20.505 | -9.647 | -14.682 | 1.00 | 31.51 | O |
| ATOM | 852 | N | SER B 485 | 21.813 | -8.507 | -13.271 | 1.00 | 29.38 | N |
| ATOM | 853 | CA | SER B 485 | 22.090 | -9.663 | -12.405 | 1.00 | 28.04 | C |
| ATOM | 855 | CB | SER B 485 | 23.534 | -9.566 | -11.893 | 1.00 | 28.80 | C |
| ATOM | 858 | OG | SER B 485 | 23.706 | -8.507 | -10.938 | 1.00 | 30.50 | O |
| ATOM | 860 | C | SER B 485 | 21.107 | -9.757 | -11.225 | 1.00 | 27.63 | C |

Figure 1L

```
ATOM    861  O   SER B 485      21.023 -10.792 -10.551  1.00 30.00           O
ATOM    863  N   ASP B 486      20.356  -8.692 -10.972  1.00 23.63           N
ATOM    864  CA  ASP B 486      19.512  -8.591  -9.797  1.00 22.00           C
ATOM    866  CB  ASP B 486      20.360  -8.472  -8.505  1.00 21.12           C
ATOM    869  CG  ASP B 486      21.313  -7.275  -8.512  1.00 20.59           C
ATOM    870  OD1 ASP B 486      20.989  -6.246  -9.186  1.00 19.03           O
ATOM    871  OD2 ASP B 486      22.385  -7.349  -7.920  1.00 18.91           O
ATOM    872  C   ASP B 486      18.568  -7.392  -9.905  1.00 20.78           C
ATOM    873  O   ASP B 486      18.507  -6.751 -10.971  1.00 19.93           O
ATOM    875  N   GLU B 487      17.788  -7.123  -8.876  1.00 19.48           N
ATOM    876  CA  GLU B 487      16.783  -6.071  -8.894  1.00 18.79           C
ATOM    878  CB  GLU B 487      15.794  -6.211  -7.758  1.00 20.93           C
ATOM    881  CG  GLU B 487      16.308  -5.796  -6.410  1.00 20.11           C
ATOM    884  CD  GLU B 487      17.323  -6.743  -5.795  1.00 22.35           C
ATOM    885  OE1 GLU B 487      17.637  -7.832  -6.355  1.00 24.79           O
ATOM    886  OE2 GLU B 487      17.858  -6.431  -4.695  1.00 22.86           O
ATOM    887  C   GLU B 487      17.401  -4.667  -8.934  1.00 18.54           C
ATOM    888  O   GLU B 487      16.733  -3.717  -9.359  1.00 18.99           O
ATOM    890  N   PHE B 488      18.632  -4.531  -8.451  1.00 16.77           N
ATOM    891  CA  PHE B 488      19.298  -3.226  -8.480  1.00 16.41           C
ATOM    893  CB  PHE B 488      20.576  -3.264  -7.667  1.00 15.57           C
ATOM    896  CG  PHE B 488      21.326  -1.966  -7.662  1.00 13.97           C
ATOM    897  CD1 PHE B 488      21.201  -1.074  -6.640  1.00 15.58           C
ATOM    899  CE1 PHE B 488      21.884   0.121  -6.687  1.00 13.94           C
ATOM    901  CZ  PHE B 488      22.678   0.425  -7.746  1.00 14.70           C
ATOM    903  CE2 PHE B 488      22.800  -0.430  -8.784  1.00 15.86           C
ATOM    905  CD2 PHE B 488      22.153  -1.635  -8.743  1.00 14.34           C
ATOM    907  C   PHE B 488      19.611  -2.940  -9.935  1.00 15.60           C
ATOM    908  O   PHE B 488      19.245  -1.853 -10.458  1.00 15.88           O
ATOM    910  N   ASP B 489      20.224  -3.903 -10.632  1.00 15.92           N
ATOM    911  CA  ASP B 489      20.499  -3.760 -12.050  1.00 16.83           C
ATOM    913  CB  ASP B 489      21.267  -4.958 -12.599  1.00 16.37           C
ATOM    916  CG  ASP B 489      22.609  -5.173 -11.984  1.00 20.61           C
ATOM    917  OD1 ASP B 489      23.099  -4.366 -11.155  1.00 19.89           O
ATOM    918  OD2 ASP B 489      23.225  -6.224 -12.376  1.00 23.35           O
ATOM    919  C   ASP B 489      19.215  -3.580 -12.867  1.00 16.28           C
ATOM    920  O   ASP B 489      19.145  -2.771 -13.797  1.00 17.25           O
ATOM    922  N   ALA B 490      18.156  -4.273 -12.518  1.00 16.50           N
```

Figure 1M

| ATOM | 923 | CA | ALA B 490 | 16.866 | -4.100 | -13.223 | 1.00 | 17.23 | C |
| ATOM | 925 | CB | ALA B 490 | 15.834 | -5.113 | -12.743 | 1.00 | 19.05 | C |
| ATOM | 929 | C | ALA B 490 | 16.322 | -2.678 | -13.050 | 1.00 | 17.71 | C |
| ATOM | 930 | O | ALA B 490 | 15.783 | -2.095 | -13.993 | 1.00 | 18.28 | O |
| ATOM | 932 | N | SER B 491 | 16.457 | -2.098 | -11.865 | 1.00 | 16.17 | N |
| ATOM | 933 | CA | SER B 491 | 16.078 | -0.702 | -11.651 | 1.00 | 15.93 | C |
| ATOM | 935 | CB | SER B 491 | 16.249 | -0.353 | -10.174 | 1.00 | 16.85 | C |
| ATOM | 938 | OG | SER B 491 | 15.256 | -1.024 | -9.414 | 1.00 | 20.83 | O |
| ATOM | 940 | C | SER B 491 | 16.938 | 0.261 | -12.477 | 1.00 | 15.87 | C |
| ATOM | 941 | O | SER B 491 | 16.405 | 1.225 | -13.047 | 1.00 | 14.96 | O |
| ATOM | 943 | N | ILE B 492 | 18.225 | 0.008 | -12.598 | 1.00 | 15.71 | N |
| ATOM | 944 | CA | ILE B 492 | 19.092 | 0.803 | -13.430 | 1.00 | 16.55 | C |
| ATOM | 946 | CB | ILE B 492 | 20.558 | 0.339 | -13.309 | 1.00 | 16.36 | C |
| ATOM | 948 | CG1 | ILE B 492 | 21.114 | 0.632 | -11.904 | 1.00 | 17.32 | C |
| ATOM | 951 | CD1 | ILE B 492 | 21.305 | 2.129 | -11.573 | 1.00 | 19.14 | C |
| ATOM | 955 | CG2 | ILE B 492 | 21.464 | 0.934 | -14.361 | 1.00 | 15.94 | C |
| ATOM | 959 | C | ILE B 492 | 18.598 | 0.746 | -14.901 | 1.00 | 16.78 | C |
| ATOM | 960 | O | ILE B 492 | 18.532 | 1.758 | -15.615 | 1.00 | 16.72 | O |
| ATOM | 962 | N | SER B 493 | 18.227 | -0.445 | -15.366 | 1.00 | 17.10 | N |
| ATOM | 963 | CA | ASER B 493 | 17.674 | -0.612 | -16.701 | 0.50 | 17.91 | C |
| ATOM | 964 | CA | BSER B 493 | 17.678 | -0.588 | -16.707 | 0.50 | 18.13 | C |
| ATOM | 967 | CB | ASER B 493 | 17.360 | -2.091 | -16.965 | 0.50 | 18.67 | C |
| ATOM | 968 | CB | BSER B 493 | 17.409 | -2.057 | -17.012 | 0.50 | 19.07 | C |
| ATOM | 973 | OG | ASER B 493 | 17.016 | -2.276 | -18.322 | 0.50 | 19.94 | O |
| ATOM | 974 | OG | BSER B 493 | 18.638 | -2.726 | -17.045 | 0.50 | 22.21 | O |
| ATOM | 977 | C | SER B 493 | 16.410 | 0.210 | -16.871 | 1.00 | 18.07 | C |
| ATOM | 978 | O | SER B 493 | 16.188 | 0.790 | -17.932 | 1.00 | 18.35 | O |
| ATOM | 980 | N | GLN B 494 | 15.567 | 0.265 | -15.856 | 1.00 | 16.85 | N |
| ATOM | 981 | CA | GLN B 494 | 14.353 | 1.041 | -15.877 | 1.00 | 17.80 | C |
| ATOM | 983 | CB | GLN B 494 | 13.543 | 0.813 | -14.620 | 1.00 | 19.96 | C |
| ATOM | 986 | CG | GLN B 494 | 12.236 | 1.497 | -14.564 | 1.00 | 23.31 | C |
| ATOM | 989 | CD | GLN B 494 | 11.495 | 1.240 | -13.260 | 1.00 | 26.42 | C |
| ATOM | 990 | OE1 | GLN B 494 | 12.100 | 0.774 | -12.255 | 1.00 | 37.03 | O |
| ATOM | 991 | NE2 | GLN B 494 | 10.174 | 1.537 | -13.247 | 1.00 | 33.65 | N |
| ATOM | 994 | C | GLN B 494 | 14.710 | 2.533 | -16.005 | 1.00 | 16.11 | C |
| ATOM | 995 | O | GLN B 494 | 14.007 | 3.280 | -16.725 | 1.00 | 15.87 | O |
| ATOM | 997 | N | VAL B 495 | 15.743 | 3.002 | -15.303 | 1.00 | 14.39 | N |
| ATOM | 998 | CA | VAL B 495 | 16.142 | 4.412 | -15.448 | 1.00 | 15.23 | C |

Figure 1N

| ATOM | 1000 | CB | VAL B 495 | 17.332 | 4.757 | -14.551 | 1.00 | 13.69 | C |
| --- | --- | --- | --- | --- | --- | --- | --- | --- | --- |
| ATOM | 1002 | CG1 | VAL B 495 | 17.738 | 6.185 | -14.762 | 1.00 | 14.25 | C |
| ATOM | 1006 | CG2 | VAL B 495 | 16.978 | 4.588 | -13.068 | 1.00 | 15.90 | C |
| ATOM | 1010 | C | VAL B 495 | 16.510 | 4.657 | -16.907 | 1.00 | 14.79 | C |
| ATOM | 1011 | O | VAL B 495 | 16.080 | 5.672 | -17.513 | 1.00 | 13.37 | O |
| ATOM | 1013 | N | ASN B 496 | 17.303 | 3.775 | -17.505 | 1.00 | 14.68 | N |
| ATOM | 1014 | CA | ASN B 496 | 17.685 | 3.925 | -18.892 | 1.00 | 15.95 | C |
| ATOM | 1016 | CB | ASN B 496 | 18.722 | 2.903 | -19.357 | 1.00 | 16.06 | C |
| ATOM | 1019 | CG | ASN B 496 | 20.041 | 3.097 | -18.740 | 1.00 | 20.64 | C |
| ATOM | 1020 | OD1 | ASN B 496 | 20.490 | 4.232 | -18.582 | 1.00 | 22.95 | O |
| ATOM | 1021 | ND2 | ASN B 496 | 20.740 | 1.986 | -18.479 | 1.00 | 24.48 | N |
| ATOM | 1024 | C | ASN B 496 | 16.434 | 3.921 | -19.795 | 1.00 | 14.49 | C |
| ATOM | 1025 | O | ASN B 496 | 16.367 | 4.745 | -20.736 | 1.00 | 14.54 | O |
| ATOM | 1027 | N | GLU B 497 | 15.440 | 3.094 | -19.521 | 1.00 | 14.98 | N |
| ATOM | 1028 | CA | AGLU B 497 | 14.232 | 3.104 | -20.337 | 0.50 | 16.38 | C |
| ATOM | 1029 | CA | BGLU B 497 | 14.195 | 3.092 | -20.297 | 0.50 | 16.29 | C |
| ATOM | 1032 | CB | AGLU B 497 | 13.283 | 1.968 | -19.966 | 0.50 | 16.85 | C |
| ATOM | 1033 | CB | BGLU B 497 | 13.226 | 2.017 | -19.791 | 0.50 | 17.52 | C |
| ATOM | 1038 | CG | AGLU B 497 | 13.844 | 0.549 | -20.205 | 0.50 | 18.95 | C |
| ATOM | 1039 | CG | BGLU B 497 | 11.834 | 1.991 | -20.443 | 0.50 | 18.00 | C |
| ATOM | 1044 | CD | AGLU B 497 | 13.108 | -0.173 | -21.322 | 0.50 | 22.35 | C |
| ATOM | 1045 | CD | BGLU B 497 | 10.914 | 0.933 | -19.832 | 0.50 | 21.03 | C |
| ATOM | 1046 | OE1 | AGLU B 497 | 11.883 | -0.401 | -21.151 | 0.50 | 28.91 | O |
| ATOM | 1047 | OE1 | BGLU B 497 | 11.414 | -0.004 | -19.156 | 0.50 | 31.89 | O |
| ATOM | 1048 | OE2 | AGLU B 497 | 13.737 | -0.472 | -22.343 | 0.50 | 30.08 | O |
| ATOM | 1049 | OE2 | BGLU B 497 | 9.682 | 1.055 | -20.011 | 0.50 | 26.88 | O |
| ATOM | 1050 | C | GLU B 497 | 13.515 | 4.436 | -20.218 | 1.00 | 15.27 | C |
| ATOM | 1051 | O | GLU B 497 | 13.030 | 4.957 | -21.213 | 1.00 | 15.91 | O |
| ATOM | 1053 | N | LYS B 498 | 13.433 | 5.020 | -19.018 | 1.00 | 13.99 | N |
| ATOM | 1054 | CA | LYS B 498 | 12.828 | 6.337 | -18.839 | 1.00 | 14.80 | C |
| ATOM | 1056 | CB | LYS B 498 | 12.633 | 6.638 | -17.341 | 1.00 | 17.13 | C |
| ATOM | 1059 | CG | LYS B 498 | 11.571 | 5.739 | -16.666 | 1.00 | 18.99 | C |
| ATOM | 1062 | CD | LYS B 498 | 10.157 | 6.252 | -17.059 | 1.00 | 25.04 | C |
| ATOM | 1065 | CE | LYS B 498 | 9.052 | 5.236 | -16.911 | 1.00 | 30.01 | C |
| ATOM | 1068 | NZ | LYS B 498 | 7.889 | 5.695 | -17.740 | 1.00 | 32.44 | N |
| ATOM | 1072 | C | LYS B 498 | 13.603 | 7.469 | -19.518 | 1.00 | 14.31 | C |
| ATOM | 1073 | O | LYS B 498 | 12.959 | 8.392 | -20.083 | 1.00 | 13.66 | O |
| ATOM | 1075 | N | ILE B 499 | 14.919 | 7.405 | -19.545 | 1.00 | 13.23 | N |

Figure 10

| ATOM | 1076 | CA | ILE B 499 | 15.698 | 8.359 | -20.295 | 1.00 | 13.81 | C |
| --- | --- | --- | --- | --- | --- | --- | --- | --- | --- |
| ATOM | 1078 | CB | ILE B 499 | 17.159 | 8.182 | -20.034 | 1.00 | 14.41 | C |
| ATOM | 1080 | CG1 | ILE B 499 | 17.547 | 8.510 | -18.584 | 1.00 | 14.68 | C |
| ATOM | 1083 | CD1 | ILE B 499 | 18.892 | 7.936 | -18.176 | 1.00 | 16.19 | C |
| ATOM | 1087 | CG2 | ILE B 499 | 17.985 | 9.032 | -20.987 | 1.00 | 16.50 | C |
| ATOM | 1091 | C | ILE B 499 | 15.356 | 8.225 | -21.786 | 1.00 | 14.64 | C |
| ATOM | 1092 | O | ILE B 499 | 15.117 | 9.238 | -22.484 | 1.00 | 14.35 | O |
| ATOM | 1094 | N | ASN B 500 | 15.260 | 7.001 | -22.282 | 1.00 | 13.76 | N |
| ATOM | 1095 | CA | ASN B 500 | 14.961 | 6.803 | -23.718 | 1.00 | 15.25 | C |
| ATOM | 1097 | CB | ASN B 500 | 15.119 | 5.329 | -24.106 | 1.00 | 16.08 | C |
| ATOM | 1100 | CG | ASN B 500 | 16.531 | 4.938 | -24.180 | 1.00 | 19.34 | C |
| ATOM | 1101 | OD1 | ASN B 500 | 17.419 | 5.756 | -24.316 | 1.00 | 23.45 | O |
| ATOM | 1102 | ND2 | ASN B 500 | 16.770 | 3.634 | -24.117 | 1.00 | 23.20 | N |
| ATOM | 1105 | C | ASN B 500 | 13.547 | 7.285 | -24.031 | 1.00 | 14.17 | C |
| ATOM | 1106 | O | ASN B 500 | 13.319 | 7.867 | -25.107 | 1.00 | 14.87 | O |
| ATOM | 1108 | N | GLN B 501 | 12.614 | 7.110 | -23.153 | 1.00 | 13.91 | N |
| ATOM | 1109 | CA | GLN B 501 | 11.247 | 7.625 | -23.320 | 1.00 | 15.07 | C |
| ATOM | 1111 | CB | GLN B 501 | 10.291 | 7.137 | -22.231 | 1.00 | 16.35 | C |
| ATOM | 1114 | CG | GLN B 501 | 9.947 | 5.697 | -22.405 | 1.00 | 20.19 | C |
| ATOM | 1117 | CD | GLN B 501 | 9.121 | 5.129 | -21.273 | 1.00 | 22.58 | C |
| ATOM | 1118 | OE1 | GLN B 501 | 9.421 | 5.354 | -20.106 | 1.00 | 26.92 | O |
| ATOM | 1119 | NE2 | GLN B 501 | 8.076 | 4.399 | -21.600 | 1.00 | 26.11 | N |
| ATOM | 1122 | C | GLN B 501 | 11.243 | 9.153 | -23.379 | 1.00 | 15.10 | C |
| ATOM | 1123 | O | GLN B 501 | 10.555 | 9.756 | -24.197 | 1.00 | 15.99 | O |
| ATOM | 1125 | N | SER B 502 | 12.013 | 9.791 | -22.486 | 1.00 | 14.43 | N |
| ATOM | 1126 | CA | SER B 502 | 12.184 | 11.221 | -22.494 | 1.00 | 14.39 | C |
| ATOM | 1128 | CB | SER B 502 | 13.135 | 11.636 | -21.378 | 1.00 | 13.33 | C |
| ATOM | 1131 | OG | SER B 502 | 13.303 | 13.030 | -21.324 | 1.00 | 18.59 | O |
| ATOM | 1133 | C | SER B 502 | 12.688 | 11.711 | -23.848 | 1.00 | 14.07 | C |
| ATOM | 1134 | O | SER B 502 | 12.087 | 12.629 | -24.441 | 1.00 | 14.51 | O |
| ATOM | 1136 | N | LEU B 503 | 13.766 | 11.112 | -24.317 | 1.00 | 13.99 | N |
| ATOM | 1137 | CA | LEU B 503 | 14.348 | 11.505 | -25.602 | 1.00 | 14.44 | C |
| ATOM | 1139 | CB | LEU B 503 | 15.650 | 10.740 | -25.858 | 1.00 | 14.48 | C |
| ATOM | 1142 | CG | LEU B 503 | 16.780 | 11.075 | -24.872 | 1.00 | 16.13 | C |
| ATOM | 1144 | CD1 | LEU B 503 | 17.937 | 10.142 | -25.020 | 1.00 | 19.77 | C |
| ATOM | 1148 | CD2 | LEU B 503 | 17.274 | 12.514 | -25.097 | 1.00 | 16.47 | C |
| ATOM | 1152 | C | LEU B 503 | 13.361 | 11.296 | -26.732 | 1.00 | 14.95 | C |
| ATOM | 1153 | O | LEU B 503 | 13.295 | 12.127 | -27.673 | 1.00 | 15.08 | O |

Figure 1P

| ATOM | 1155 | N | ALA B 504 | 12.554 | 10.249 | -26.677 | 1.00 | 13.94 | N |
| ATOM | 1156 | CA | ALA B 504 | 11.526 | 9.979 | -27.694 | 1.00 | 14.59 | C |
| ATOM | 1158 | CB | ALA B 504 | 10.879 | 8.654 | -27.426 | 1.00 | 15.11 | C |
| ATOM | 1162 | C | ALA B 504 | 10.460 | 11.042 | -27.738 | 1.00 | 14.51 | C |
| ATOM | 1163 | O | ALA B 504 | 10.033 | 11.506 | -28.814 | 1.00 | 15.17 | O |
| ATOM | 1165 | N | PHE B 505 | 9.958 | 11.448 | -26.581 | 1.00 | 14.30 | N |
| ATOM | 1166 | CA | PHE B 505 | 8.994 | 12.546 | -26.481 | 1.00 | 15.14 | C |
| ATOM | 1168 | CB | PHE B 505 | 8.446 | 12.683 | -25.060 | 1.00 | 15.81 | C |
| ATOM | 1171 | CG | PHE B 505 | 7.424 | 11.616 | -24.669 | 1.00 | 17.35 | C |
| ATOM | 1172 | CD1 | PHE B 505 | 7.625 | 10.835 | -23.516 | 1.00 | 19.38 | C |
| ATOM | 1174 | CE1 | PHE B 505 | 6.693 | 9.894 | -23.126 | 1.00 | 20.10 | C |
| ATOM | 1176 | CZ | PHE B 505 | 5.502 | 9.768 | -23.838 | 1.00 | 23.17 | C |
| ATOM | 1178 | CE2 | PHE B 505 | 5.264 | 10.571 | -24.957 | 1.00 | 21.38 | C |
| ATOM | 1180 | CD2 | PHE B 505 | 6.214 | 11.481 | -25.367 | 1.00 | 20.42 | C |
| ATOM | 1182 | C | PHE B 505 | 9.582 | 13.894 | -26.954 | 1.00 | 14.38 | C |
| ATOM | 1183 | O | PHE B 505 | 8.870 | 14.669 | -27.617 | 1.00 | 14.37 | O |
| ATOM | 1185 | N | ILE B 506 | 10.852 | 14.175 | -26.687 | 1.00 | 13.87 | N |
| ATOM | 1186 | CA | ILE B 506 | 11.491 | 15.346 | -27.246 | 1.00 | 13.99 | C |
| ATOM | 1188 | CB | ILE B 506 | 12.847 | 15.615 | -26.616 | 1.00 | 13.35 | C |
| ATOM | 1190 | CG1 | ILE B 506 | 12.717 | 15.939 | -25.115 | 1.00 | 14.38 | C |
| ATOM | 1193 | CD1 | ILE B 506 | 11.811 | 17.123 | -24.759 | 1.00 | 14.37 | C |
| ATOM | 1197 | CG2 | ILE B 506 | 13.482 | 16.815 | -27.329 | 1.00 | 14.49 | C |
| ATOM | 1201 | C | ILE B 506 | 11.565 | 15.223 | -28.775 | 1.00 | 14.82 | C |
| ATOM | 1202 | O | ILE B 506 | 11.288 | 16.241 | -29.473 | 1.00 | 14.67 | O |
| ATOM | 1204 | N | ARG B 507 | 11.897 | 14.063 | -29.300 | 1.00 | 15.29 | N |
| ATOM | 1205 | CA | ARG B 507 | 11.961 | 13.893 | -30.750 | 1.00 | 15.44 | C |
| ATOM | 1207 | CB | ARG B 507 | 12.379 | 12.469 | -31.115 | 1.00 | 16.74 | C |
| ATOM | 1210 | CG | ARG B 507 | 12.398 | 12.273 | -32.642 | 1.00 | 17.16 | C |
| ATOM | 1213 | CD | ARG B 507 | 12.912 | 10.891 | -33.033 | 1.00 | 19.00 | C |
| ATOM | 1216 | NE | ARG B 507 | 12.618 | 10.761 | -34.466 | 1.00 | 19.75 | N |
| ATOM | 1218 | CZ | ARG B 507 | 12.849 | 9.679 | -35.182 | 1.00 | 20.23 | C |
| ATOM | 1219 | NH1 | ARG B 507 | 13.389 | 8.628 | -34.600 | 1.00 | 20.44 | N |
| ATOM | 1222 | NH2 | ARG B 507 | 12.501 | 9.676 | -36.462 | 1.00 | 22.42 | N |
| ATOM | 1225 | C | ARG B 507 | 10.633 | 14.268 | -31.341 | 1.00 | 15.26 | C |
| ATOM | 1226 | O | ARG B 507 | 10.596 | 14.997 | -32.364 | 1.00 | 16.99 | O |
| ATOM | 1228 | N | LYS B 508 | 9.553 | 13.771 | -30.799 | 1.00 | 16.37 | N |
| ATOM | 1229 | CA | LYS B 508 | 8.240 | 14.062 | -31.318 | 1.00 | 15.79 | C |
| ATOM | 1231 | CB | LYS B 508 | 7.163 | 13.273 | -30.590 | 1.00 | 17.78 | C |

Figure 1Q

| | | | | | | | | | |
|---|---|---|---|---|---|---|---|---|---|
| ATOM | 1234 | CG | LYS B 508 | 5.772 | 13.523 | -31.072 | 1.00 | 19.88 | C |
| ATOM | 1237 | CD | LYS B 508 | 5.551 | 13.266 | -32.549 | 1.00 | 24.16 | C |
| ATOM | 1240 | CE | LYS B 508 | 4.043 | 13.208 | -32.880 | 1.00 | 25.79 | C |
| ATOM | 1243 | NZ | LYS B 508 | 3.328 | 11.990 | -32.355 | 1.00 | 30.58 | N |
| ATOM | 1247 | C | LYS B 508 | 7.943 | 15.550 | -31.252 | 1.00 | 16.60 | C |
| ATOM | 1248 | O | LYS B 508 | 7.435 | 16.139 | -32.209 | 1.00 | 17.35 | O |
| ATOM | 1250 | N | SER B 509 | 8.262 | 16.210 | -30.141 | 1.00 | 15.51 | N |
| ATOM | 1251 | CA | SER B 509 | 8.069 | 17.635 | -30.016 | 1.00 | 15.97 | C |
| ATOM | 1253 | CB | SER B 509 | 8.483 | 18.058 | -28.607 | 1.00 | 14.71 | C |
| ATOM | 1256 | OG | SER B 509 | 8.348 | 19.487 | -28.435 | 1.00 | 14.92 | O |
| ATOM | 1258 | C | SER B 509 | 8.865 | 18.395 | -31.072 | 1.00 | 15.93 | C |
| ATOM | 1259 | O | SER B 509 | 8.292 | 19.269 | -31.754 | 1.00 | 17.30 | O |
| ATOM | 1261 | N | ASP B 510 | 10.121 | 18.088 | -31.227 | 1.00 | 16.05 | N |
| ATOM | 1262 | CA | ASP B 510 | 10.994 | 18.704 | -32.253 | 1.00 | 17.43 | C |
| ATOM | 1264 | CB | ASP B 510 | 12.431 | 18.167 | -32.251 | 1.00 | 17.08 | C |
| ATOM | 1267 | CG | ASP B 510 | 13.270 | 18.683 | -31.123 | 1.00 | 20.91 | C |
| ATOM | 1268 | OD1 | ASP B 510 | 13.003 | 19.775 | -30.560 | 1.00 | 23.16 | O |
| ATOM | 1269 | OD2 | ASP B 510 | 14.296 | 17.994 | -30.834 | 1.00 | 23.49 | O |
| ATOM | 1270 | C | ASP B 510 | 10.403 | 18.539 | -33.649 | 1.00 | 19.67 | C |
| ATOM | 1271 | O | ASP B 510 | 10.466 | 19.478 | -34.450 | 1.00 | 20.27 | O |
| ATOM | 1273 | N | GLU B 511 | 9.907 | 17.350 | -33.968 | 1.00 | 19.17 | N |
| ATOM | 1274 | CA | GLU B 511 | 9.340 | 17.049 | -35.299 | 1.00 | 20.26 | C |
| ATOM | 1276 | CB | GLU B 511 | 9.062 | 15.524 | -35.420 | 1.00 | 19.28 | C |
| ATOM | 1279 | CG | GLU B 511 | 10.319 | 14.727 | -35.595 | 1.00 | 20.10 | C |
| ATOM | 1282 | CD | GLU B 511 | 10.139 | 13.219 | -35.636 | 1.00 | 19.95 | C |
| ATOM | 1283 | OE1 | GLU B 511 | 9.037 | 12.729 | -35.315 | 1.00 | 20.57 | O |
| ATOM | 1284 | OE2 | GLU B 511 | 11.166 | 12.615 | -36.006 | 1.00 | 21.69 | O |
| ATOM | 1285 | C | GLU B 511 | 8.108 | 17.885 | -35.556 | 1.00 | 20.65 | C |
| ATOM | 1286 | O | GLU B 511 | 7.976 | 18.450 | -36.687 | 1.00 | 21.86 | O |
| ATOM | 1288 | N | LEU B 512 | 7.208 | 18.020 | -34.576 | 1.00 | 21.55 | N |
| ATOM | 1289 | CA | LEU B 512 | 6.048 | 18.927 | -34.656 | 1.00 | 22.97 | C |
| ATOM | 1291 | CB | LEU B 512 | 5.159 | 18.820 | -33.413 | 1.00 | 23.31 | C |
| ATOM | 1294 | CG | LEU B 512 | 4.419 | 17.485 | -33.311 | 1.00 | 23.70 | C |
| ATOM | 1296 | CD1 | LEU B 512 | 3.955 | 17.157 | -31.910 | 1.00 | 24.56 | C |
| ATOM | 1300 | CD2 | LEU B 512 | 3.220 | 17.435 | -34.275 | 1.00 | 26.99 | C |
| ATOM | 1304 | C | LEU B 512 | 6.473 | 20.385 | -34.886 | 1.00 | 23.64 | C |
| ATOM | 1305 | O | LEU B 512 | 5.860 | 21.072 | -35.713 | 1.00 | 25.92 | O |
| ATOM | 1307 | N | LEU B 513 | 7.518 | 20.854 | -34.229 | 1.00 | 23.38 | N |

Figure 1R

```
ATOM   1308  CA   LEU B 513       7.976  22.245 -34.371  1.00 26.06           C
ATOM   1310  CB   LEU B 513       8.943  22.616 -33.250  1.00 25.20           C
ATOM   1313  CG   LEU B 513       8.244  22.636 -31.890  1.00 23.84           C
ATOM   1315  CD1  LEU B 513       9.285  22.729 -30.807  1.00 24.84           C
ATOM   1319  CD2  LEU B 513       7.156  23.758 -31.817  1.00 25.18           C
ATOM   1323  C    LEU B 513       8.651  22.519 -35.712  1.00 28.36           C
ATOM   1324  O    LEU B 513       8.551  23.636 -36.244  1.00 27.91           O
ATOM   1326  N    HIS B 514       9.338  21.532 -36.262  1.00 31.31           N
ATOM   1327  CA   HIS B 514      10.032  21.733 -37.531  1.00 33.78           C
ATOM   1329  CB   HIS B 514      11.114  20.702 -37.731  1.00 34.92           C
ATOM   1332  CG   HIS B 514      12.226  20.829 -36.738  1.00 36.97           C
ATOM   1333  ND1  HIS B 514      12.760  22.047 -36.372  1.00 40.90           N
ATOM   1335  CE1  HIS B 514      13.708  21.855 -35.470  1.00 39.12           C
ATOM   1337  NE2  HIS B 514      13.816  20.555 -35.251  1.00 40.70           N
ATOM   1339  CD2  HIS B 514      12.905  19.892 -36.035  1.00 39.64           C
ATOM   1341  C    HIS B 514       9.015  21.749 -38.652  1.00 35.83           C
ATOM   1342  O    HIS B 514       9.340  22.140 -39.762  1.00 37.84           O
ATOM   1344  N    ASN B 515       7.779  21.375 -38.331  1.00 37.85           N
ATOM   1345  CA   ASN B 515       6.624  21.526 -39.207  1.00 39.08           C
ATOM   1347  CB   ASN B 515       5.689  20.340 -38.964  1.00 39.57           C
ATOM   1350  CG   ASN B 515       4.748  20.105 -40.109  1.00 40.27           C
ATOM   1351  OD1  ASN B 515       5.176  20.032 -41.272  1.00 46.15           O
ATOM   1352  ND2  ASN B 515       3.457  19.983 -39.804  1.00 41.42           N
ATOM   1355  C    ASN B 515       5.831  22.842 -39.004  1.00 39.97           C
ATOM   1356  O    ASN B 515       4.791  23.050 -39.646  1.00 40.63           O
ATOM   1358  N    VAL B 516       6.293  23.715 -38.103  1.00 40.23           N
ATOM   1359  CA   VAL B 516       5.637  24.999 -37.852  1.00 41.24           C
ATOM   1361  CB   VAL B 516       5.675  25.375 -36.349  1.00 41.07           C
ATOM   1363  CG1  VAL B 516       5.270  26.846 -36.120  1.00 41.12           C
ATOM   1367  CG2  VAL B 516       4.771  24.457 -35.570  1.00 40.80           C
ATOM   1371  C    VAL B 516       6.292  26.108 -38.689  1.00 42.00           C
ATOM   1372  O    VAL B 516       7.523  26.169 -38.826  1.00 42.16           O
ATOM   1374  N    ASN B 517       5.441  26.961 -39.262  1.00 43.15           N
ATOM   1375  CA   ASN B 517       5.857  28.187 -39.940  1.00 43.21           C
ATOM   1377  CB   ASN B 517       5.856  27.980 -41.456  1.00 44.08           C
ATOM   1383  C    ASN B 517       4.907  29.328 -39.568  1.00 43.86           C
ATOM   1384  O    ASN B 517       5.105  30.034 -38.568  1.00 44.53           O
ATOM   1386  O56  TTZ Z   1      24.455  -6.787  -4.924  1.00 18.37           O
```

Figure 1S

| | | | | | | | | | | |
|---|---|---|---|---|---|---|---|---|---|---|
| ATOM | 1388 | C45 | TTZ | Z | 1 | 23.943 | -5.608 | -4.457 | 1.00 16.47 | C |
| ATOM | 1389 | C46 | TTZ | Z | 1 | 24.733 | -4.515 | -4.179 | 1.00 17.08 | C |
| ATOM | 1391 | C47 | TTZ | Z | 1 | 24.056 | -3.355 | -3.725 | 1.00 15.21 | C |
| ATOM | 1393 | C48 | TTZ | Z | 1 | 22.681 | -3.312 | -3.631 | 1.00 16.54 | C |
| ATOM | 1394 | C58 | TTZ | Z | 1 | 21.956 | -2.070 | -3.161 | 1.00 16.64 | C |
| ATOM | 1398 | N49 | TTZ | Z | 1 | 21.938 | -4.395 | -3.917 | 1.00 16.21 | N |
| ATOM | 1399 | C42 | TTZ | Z | 1 | 22.589 | -5.522 | -4.351 | 1.00 15.46 | C |
| ATOM | 1400 | C41 | TTZ | Z | 1 | 21.711 | -6.660 | -4.692 | 1.00 17.33 | C |
| ATOM | 1403 | N26 | TTZ | Z | 1 | 21.989 | -7.914 | -3.957 | 1.00 17.49 | N |
| ATOM | 1404 | C17 | TTZ | Z | 1 | 22.316 | -9.089 | -4.502 | 1.00 18.90 | C |
| ATOM | 1405 | N16 | TTZ | Z | 1 | 22.508 | -9.301 | -5.818 | 1.00 19.45 | N |
| ATOM | 1407 | C15 | TTZ | Z | 1 | 22.800 | -10.628 | -6.379 | 1.00 21.67 | C |
| ATOM | 1410 | C14 | TTZ | Z | 1 | 24.290 | -10.788 | -6.591 | 1.00 30.40 | C |
| ATOM | 1413 | C13 | TTZ | Z | 1 | 24.844 | -9.931 | -7.731 | 1.00 36.38 | C |
| ATOM | 1416 | N3 | TTZ | Z | 1 | 26.218 | -10.335 | -8.156 | 1.00 39.94 | N |
| ATOM | 1418 | C4 | TTZ | Z | 1 | 27.250 | -9.756 | -7.268 | 1.00 41.59 | C |
| ATOM | 1421 | C5 | TTZ | Z | 1 | 28.637 | -10.279 | -7.630 | 1.00 42.62 | C |
| ATOM | 1424 | O6 | TTZ | Z | 1 | 28.924 | -9.850 | -8.958 | 1.00 44.00 | O |
| ATOM | 1425 | C1 | TTZ | Z | 1 | 27.938 | -10.313 | -9.907 | 1.00 43.91 | C |
| ATOM | 1428 | C2 | TTZ | Z | 1 | 26.511 | -9.888 | -9.531 | 1.00 42.52 | C |
| ATOM | 1431 | N23 | TTZ | Z | 1 | 22.417 | -10.071 | -3.597 | 1.00 18.37 | N |
| ATOM | 1432 | C25 | TTZ | Z | 1 | 21.891 | -8.116 | -2.607 | 1.00 16.90 | C |
| ATOM | 1433 | C24 | TTZ | Z | 1 | 22.150 | -9.474 | -2.394 | 1.00 17.18 | C |
| ATOM | 1434 | C35 | TTZ | Z | 1 | 22.132 | -9.987 | -1.097 | 1.00 18.81 | C |
| ATOM | 1436 | C34 | TTZ | Z | 1 | 21.832 | -9.131 | -0.043 | 1.00 18.45 | C |
| ATOM | 1438 | C32 | TTZ | Z | 1 | 21.572 | -7.224 | -1.566 | 1.00 18.52 | C |
| ATOM | 1440 | C33 | TTZ | Z | 1 | 21.528 | -7.763 | -0.269 | 1.00 17.65 | C |
| ATOM | 1441 | C60 | TTZ | Z | 1 | 21.223 | -6.912 | 0.939 | 1.00 17.52 | C |
| ATOM | 1444 | N61 | TTZ | Z | 1 | 20.893 | -5.496 | 0.655 | 1.00 18.38 | N |
| ATOM | 1446 | C62 | TTZ | Z | 1 | 20.737 | -4.580 | 1.665 | 1.00 17.77 | C |
| ATOM | 1447 | C66 | TTZ | Z | 1 | 20.895 | -4.976 | 3.003 | 1.00 19.40 | C |
| ATOM | 1449 | C67 | TTZ | Z | 1 | 20.753 | -4.068 | 4.054 | 1.00 18.64 | C |
| ATOM | 1450 | C77 | TTZ | Z | 1 | 20.897 | -4.514 | 5.495 | 1.00 19.37 | C |
| ATOM | 1454 | C68 | TTZ | Z | 1 | 20.430 | -2.747 | 3.772 | 1.00 20.40 | C |
| ATOM | 1456 | C69 | TTZ | Z | 1 | 20.299 | -2.340 | 2.460 | 1.00 18.23 | C |
| ATOM | 1458 | C70 | TTZ | Z | 1 | 20.418 | -3.248 | 1.414 | 1.00 16.47 | C |
| ATOM | 1459 | C79 | TTZ | Z | 1 | 20.258 | -2.722 | -0.007 | 1.00 18.51 | C |
| ATOM | 1462 | C80 | TTZ | Z | 1 | 18.809 | -2.664 | -0.499 | 1.00 18.73 | C |

Figure 1T

| | | | | | | | | | | |
|---|---|---|---|---|---|---|---|---|---|---|
| ATOM | 1465 | C81 | TTZ | Z | 1 | 18.036 | -3.996 | -0.409 | 1.00 21.08 | C |
| ATOM | 1468 | O82 | TTZ | Z | 1 | 18.700 | -5.006 | -1.186 | 1.00 21.75 | O |
| ATOM | 1470 | O5 | PG4 | P | 1 | 29.769 | -13.982 | 2.971 | 1.00 59.67 | O |
| ATOM | 1472 | C8 | PG4 | P | 1 | 29.006 | -13.001 | 2.250 | 1.00 57.03 | C |
| ATOM | 1475 | C7 | PG4 | P | 1 | 28.104 | -12.228 | 3.212 | 1.00 56.03 | C |
| ATOM | 1478 | O4 | PG4 | P | 1 | 28.335 | -10.817 | 3.081 | 1.00 54.02 | O |
| ATOM | 1479 | C6 | PG4 | P | 1 | 27.164 | -10.013 | 2.865 | 1.00 51.19 | C |
| ATOM | 1482 | C5 | PG4 | P | 1 | 26.893 | -9.995 | 1.368 | 1.00 48.88 | C |
| ATOM | 1485 | O3 | PG4 | P | 1 | 25.819 | -9.125 | 1.018 | 1.00 47.34 | O |
| ATOM | 1486 | C4 | PG4 | P | 1 | 25.267 | -9.365 | -0.281 | 1.00 44.68 | C |
| ATOM | 1489 | C3 | PG4 | P | 1 | 26.360 | -9.542 | -1.326 | 1.00 42.77 | C |
| ATOM | 1492 | O2 | PG4 | P | 1 | 25.849 | -9.502 | -2.649 | 1.00 44.00 | O |
| ATOM | 1493 | C2 | PG4 | P | 1 | 26.888 | -9.375 | -3.614 | 1.00 45.07 | C |
| ATOM | 1496 | C1 | PG4 | P | 1 | 27.634 | -10.689 | -3.779 | 1.00 45.90 | C |
| ATOM | 1499 | O1 | PG4 | P | 1 | 29.036 | -10.495 | -3.544 | 1.00 49.66 | O |
| ATOM | 1501 | OW0 | HOH | W | 1 | 19.114 | -4.173 | -3.764 | 1.00 19.14 | O |
| ATOM | 1504 | OW0 | HOH | W | 2 | 1.613 | 16.328 | -21.387 | 1.00 21.78 | O |
| ATOM | 1507 | OW0 | HOH | W | 3 | 18.153 | -1.877 | -5.024 | 1.00 23.00 | O |
| ATOM | 1510 | OW0 | HOH | W | 4 | 16.171 | 18.880 | -29.016 | 1.00 25.39 | O |
| ATOM | 1513 | OW0 | HOH | W | 5 | 23.163 | 4.782 | -18.279 | 1.00 28.62 | O |
| ATOM | 1516 | OW0 | HOH | W | 6 | 15.650 | -2.336 | -6.810 | 1.00 28.80 | O |
| ATOM | 1519 | OW0 | HOH | W | 7 | 13.928 | 7.500 | -32.020 | 1.00 28.93 | O |
| ATOM | 1522 | OW0 | HOH | W | 8 | 20.649 | 6.039 | -20.455 | 1.00 29.63 | O |
| ATOM | 1525 | OW0 | HOH | W | 9 | 18.059 | 0.040 | 4.985 | 1.00 30.79 | O |
| ATOM | 1528 | OW0 | HOH | W | 10 | 17.667 | 1.366 | 1.392 | 1.00 34.15 | O |
| ATOM | 1531 | OW0 | HOH | W | 11 | 25.882 | -5.353 | -13.003 | 1.00 34.08 | O |
| ATOM | 1534 | OW0 | HOH | W | 12 | 15.371 | 3.339 | -1.358 | 1.00 35.76 | O |
| ATOM | 1537 | OW0 | HOH | W | 13 | 22.887 | 4.570 | 6.431 | 1.00 35.64 | O |
| ATOM | 1540 | OW0 | HOH | W | 14 | 11.996 | 3.128 | -23.247 | 1.00 35.44 | O |
| ATOM | 1543 | OW0 | HOH | W | 15 | 12.635 | 0.211 | -9.641 | 1.00 36.38 | O |
| ATOM | 1546 | OW0 | HOH | W | 16 | 23.349 | -8.034 | 6.835 | 1.00 36.75 | O |
| ATOM | 1549 | OW0 | HOH | W | 17 | 25.242 | -6.592 | 8.308 | 1.00 37.88 | O |
| ATOM | 1552 | OW0 | HOH | W | 18 | 23.627 | 2.459 | -17.455 | 1.00 38.48 | O |
| ATOM | 1555 | OW0 | HOH | W | 19 | 16.004 | 13.595 | -28.900 | 1.00 39.15 | O |
| ATOM | 1558 | OW0 | HOH | W | 20 | 14.285 | 8.952 | -29.890 | 1.00 40.85 | O |
| ATOM | 1561 | OW0 | HOH | W | 21 | 14.169 | 1.827 | -24.247 | 1.00 41.35 | O |
| ATOM | 1564 | OW0 | HOH | W | 22 | 16.435 | 4.572 | 4.401 | 1.00 41.49 | O |
| ATOM | 1567 | OW0 | HOH | W | 23 | 14.437 | 6.767 | -28.302 | 1.00 42.74 | O |

Figure 1U

```
ATOM   1570  OW0 HOH W  24    16.727   -4.640    3.638  1.00 42.99        O
ATOM   1573  OW0 HOH W  25     2.016   13.193  -18.141  1.00 43.27        O
ATOM   1576  OW0 HOH W  26    12.430   11.583  -38.733  1.00 41.62        O
ATOM   1579  OW0 HOH W  27    19.929    5.460  -22.547  1.00 44.34        O
ATOM   1582  OW0 HOH W  28     4.993   10.316  -39.370  1.00 45.13        O
ATOM   1585  OW0 HOH W  29     6.142   13.233  -35.995  1.00 48.24        O
ATOM   1588  OW0 HOH W  30    15.209   -4.665   -2.349  1.00 47.08        O
ATOM   1591  OW0 HOH W  31    -5.130   29.853  -45.272  1.00 51.12        O
ATOM   1594  OW0 HOH W  32     7.922    3.695   -9.194  1.00 50.63        O
ATOM   1597  OW0 HOH W  33     3.154   20.474  -44.313  1.00 50.50        O
ATOM   1600  OW0 HOH W  34    -3.171   20.404  -29.556  1.00 52.08        O
ATOM   1603  OW0 HOH W  35    19.807   -8.748  -13.848  1.00 41.67        O
ATOM   1606  OW0 HOH W  36    17.115   -0.855  -20.838  1.00 60.67        O
ATOM   1609  OW0 HOH W  37     6.856    7.914  -16.690  1.00 45.66        O
END
```

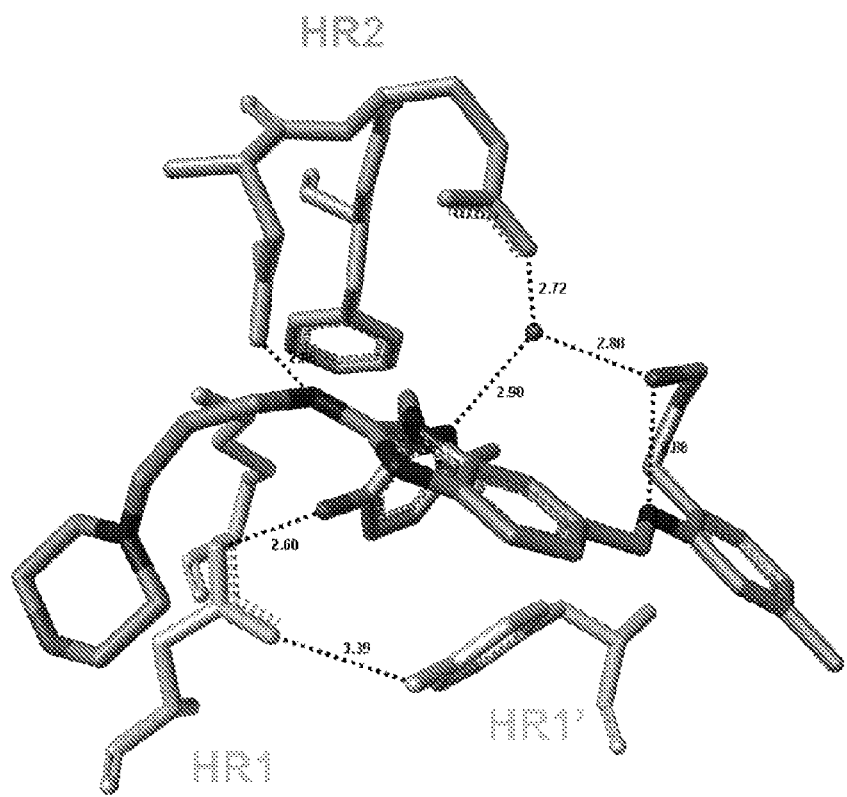
Figure 2. Schematic view of compound Z positioned in the 6HB target site.

METHODS FOR IDENTIFYING INHIBITORS AGAINST VIRUSES THAT USE A CLASS I FUSION PROTEIN

CROSS REFERENCE TO RELATED APPLICATIONS

This application is the national stage under 35 U.S.C. 371 of PCT Application No. PCT/EP2009/052307, filed Feb. 26, 2009, which application claims priority from European Patent Application No. EP 08152183.3, filed Feb. 29, 2008, the entire disclosures of which are hereby incorporated by reference in their entirety.

The invention relates to inhibitors against viruses that use a class I fusion protein, which may be effective for treating, for example, respiratory infections caused by Respiratory Syncytial Virus (RSV). More, in particular, the invention relates to the generation of a three dimensional structure of an alpha-helical coiled coil protein complex such as a six helix bundle (6HB) complexed with an inhibitor, and the use of that structure to identify, screen and/or develop new inhibitors of viruses that use a class I fusion protein, more specifically RSV.

The paramyxoviruses include many important human and animal pathogens such as measles virus, mumps virus, human RSV, human parainfluenza viruses 1-4 (hPIV 1-4), Nipah virus, Hendra virus, parainfluenza virus 5 (PIV5, also known as SV5), Newcastle disease virus (NDV) and Sendai virus.

Fusion is crucial in the life cycle of viruses using a class I fusion protein. To deliver their RNA genome into host cells, these enveloped viruses have evolved a membrane fusion mechanism that includes two surface glycoproteins: a receptor binding protein (also known as HN, H or G) and a fusion (F) protein. The fusion protein of RSV is expressed as a single precursor of 574 amino acids with several sites of N-linked glycosylation. This precursor molecule $F_o$ oligomerises in the endoplasmic reticulum and is proteolytically processed at two sites in each monomer, resulting in a trimer of two disulphide-linked fragments: $F_2$ (the smaller N-terminal fragment) and $F_1$. The protein is anchored to the virion membrane through a hydrophobic peptide in the C-terminal region of $F_1$, and is believed to adopt a metastable prefusogenic conformation until triggered in the presence of a target membrane and/or receptor. It contains two heptad repeat domains, HR1 (also known as HRA) and HR2 (also known as HRB). During fusion, a folding intermediate of the fusion protein is formed which contains a coiled-coil structure of three HR1 domains. This trimeric coiled-coil structure irreversibly refolds into a 'six-helix bundle' (6HB)-complex with three HR2 domains, juxtaposing the viral and cellular membrane.

Data from several class I fusion proteins, have indicated that the formation of such a stable 6HB is a critical event preluding the fusion of both membranes and that disturbing 6HB-formation inhibits fusion.

Respiratory Syncytial Virus (RSV) is a negative-sense, single-stranded RNA virus which belongs to the family of paramyxoviruses subfamily Pneumovirinae. Said RSV-single stranded RNA encodes for eleven viral proteins, three of which are present on the surface of the virion. These three proteins are the G, F and SH proteins. Proteins G and F are responsible for binding of the virus to target cells and fusion of the viral membrane with the target cell membrane, respectively. The F protein is apparently necessary and sufficient for viral infection to occur as mutant RSV lacking G and SH protein are still able to infect cells in vitro, albeit at a reduced level (Techaarpornkul et al. J Virology 75:6825-6834, 2001).

F is also expressed on the surface of infected cells and syncytia formation is a result of fusion of neighbouring cells mediated by the F protein.

The virus has emerged as an important human respiratory pathogen since it was first isolated from infected children in 1957. Although the virus was considered originally as a pediatric pathogen, infecting at least once virtually all children before the age of 2, immune protection is limited in time, and it is recognized now that re-infection is common in all stages of life. Generally, the infection is restricted to the upper respiratory tract and recovery is not associated with long-term pathology. However, it often progresses to a more severe lower respiratory tract infection (LRTI). For that reason, RSV is currently being considered as the most important pathogen causing LRTIs such as bronchiolitis and pneumonia in infants and young children, and it has been shown that severe RSV infections in the first year of life are a risk factor for the development of asthma later in life. The infants most at-risk of severe disease are those born prematurely, those under 6 weeks of age, those with bronchopulmonary dysplasia (BPD), and those with congenital heart disease (CHD) or immunodeficiency. In healthy adults, RSV infection usually provokes symptoms similar to the common cold, but in the elderly and immunocompromised adults, RSV pneumonia is increasingly recognized as a significant cause of morbidity and mortality. In hospitalized elderly or severely immuno-compromised with RSV pneumonia, mortality can be up to 20% and 70% respectively.

Although extensive efforts are being undertaken, a vaccine against RSV is not yet available and the development of a vaccine has been proven until now to be particularly challenging for several reasons. For instance, the initial use of formalin-inactivated vaccines was found to exacerbate rather than to prevent infection due to interactions with the patient's immune system. Treatment options are limited to a prophylactic treatment by passive immunization with a humanized monoclonal antibody (Synagis®), and to therapeutic intervention with the nucleoside analog Ribavirin. However, administration of Synagis® is only restricted to at-risk infants until the age of two, and Ribavirin treatment is limited due to its problematic mode of aerosolic administration, limited efficacy and teratogenicity. Clearly, there is a medical need for effective therapeutic options that can be applied for treatment of the whole at-risk population, including adults and the elderly.

To date, a few small molecule inhibitors of the human respiratory syncytial virus (hRSV) fusion process have been identified, so-called 6HB inhibitors, fusion inhibitors or entry inhibitors, which are believed to inhibit fusion by binding into a hydrophobic pocket that is present in each of the three grooves of the central trimeric HR1 coiled-coil in the 6HB, thereby preventing the natural HR1-HR2 interactions. However, rational 6HB inhibitor drug design in general is seriously hampered by the lack of detailed structural information on the interactions of small molecule inhibitors with their 6HB binding site.

Also, because of the molecular disorder in a solution of a peptide or peptides and a chemical compound respectively, it is currently not state of the art to successfully co-crystallize peptides with chemical small molecule compounds accordingly.

The current invention relates to the high-resolution crystal structure of a potent RSV 6HB inhibitor, also called fusion inhibitor or entry inhibitor, in complex with its binding site on the RSV fusion protein. Surprisingly, it appears that the binding pocket of the RSV 6HB inhibitor is composed of amino acid residues from both HR1 and HR2 domains. In fact, the interactions of the compound, also called 6HB inhibitor, fusion inhibitor or entry inhibitor, with HR2 strongly stabilize the binding of the compound at the surface of the HR1 trimeric coiled-coil target site, thereby destabilizing the fusion conformation of HR2. As a consequence hereof a further insight in the inhibition of the fusion mechanism with small molecules is obtained, and these new insights push forward the design and manufacturing of more effective antiviral drugs against viruses that use a class I fusion protein like Respiratory Syncytial Virus (RSV), Human Immunodeficiency Virus type 1 (HIV-1), Severe Acute Respiratory Syndrome Virus (SARS), or Ebola by allowing improved structure-based design and assay development.

The invention relates to a method for identifying an inhibitor against viruses that use a class I fusion protein comprising the steps of
  using the atomic coordinates of an alpha-helical coiled coil protein complex comprising amino acids Asp 194, Leu 195, Lys 196, Asn 197, Tyr 198, Asp 200, Lys 201, Gln 202, Leu 204, Ser 485, Asp 486, Glu 487, Phe 488, and Asp 489 according to FIG. 1±a root mean square deviation from the backbone atoms of said amino acids of not more than 1.5 Angstrom to generate a three-dimensional structure of a molecule comprising an alpha-helical coiled coil protein-like complex binding pocket;
  employing said three-dimensional structure to design or select said inhibitor.

The invention further relates to a method for identifying an inhibitor against viruses that use a class I fusion protein comprising the steps of
  using the atomic coordinates of an alpha-helical coiled coil protein complex comprising amino acids Tyr 198, Asp 200, Asp 486, Glu 487 and Phe 488 according to FIG. 1±a root mean square deviation from the backbone atoms of said amino acids of not more than 1.5 Angstrom to generate a three-dimensional structure of a molecule comprising an alpha-helical coiled coil protein-like complex binding pocket;
  employing said three-dimensional structure to design or select said inhibitor.

The invention further relates to a method for identifying an inhibitor against viruses that use a class I fusion protein, such as RSV, wherein said alpha-helical coiled coil protein complex is a 6HB characteristic for said viruses that use a class I fusion protein and wherein said inhibitor has the following interactions with heptad-region 1 (HR1) of said 6HB:
a hydrogen bond between the hydroxypyridine moiety of said inhibitor and the side chain of Asp 200 of said HR1;
a parallel pi-pi stacking between the hydroxypyridine moiety of said inhibitor and the side chain of Tyr 198 of said HR1;
a perpendicular pi-pi stacking between the benzimidazole group of said inhibitor and the side chain of Tyr 198 of said HR1 and
hydrophobic interactions between the aniline moiety of said inhibitor and HR1.

A further aspect of the current invention concerns a method for identifying an inhibitor against viruses that use a class I fusion protein further comprising between the heptad-region 2 (HR2) of said 6HB and said inhibitor the following interactions:
a hydrogen bond between the amino-group, located between the propylmorpholino moiety and the benzimidazole ring of said inhibitor, and the side chain of Asp 486 of said HR2;
a structured water mediated hydrogen bonding network formed between the sidechain of Glu 487 of said HR2 and the propanol hydroxyl and the hydroxypyridine nitrogen of said inhibitor and a parallel pi-pi stacking between the benzimidazole ring of said inhibitor and the side chain of Phe 488 of said HR2.

Part of the invention is the method as above-mentioned wherein the inhibitor is an RSV entry or fusion inhibitor with chemical name 2-[6-{[2-(3-hydroxy-propyl)-5-methyl-phenylamino]-methyl}-2-(3-morpholin-4-yl-propylamino)-benzoimidazol-1-ylmethyl]-6-methyl-pyridin-3-ol also called hereafter compound Z and having the structural formula (I)

(I)

and wherein said 6HB comprises the N52 amino acid sequence SEQ ID NO: 1 or fragments thereof and the C39 amino acid sequence SEQ ID NO: 2 or fragments thereof respectively.

The N52 amino acid sequence (also designated as NdeI) has a SEQ ID NO 1: as follows:
AHLEGEVNKIKSALLSTNKAVVSL-SNGVSVLTSKVLDLKNYIDKQLLPIVNK.

The C39 amino acid sequence has a SEQ ID NO:2 as follows:
VFPSDEFDASISQVNEKINQSLAFIRKS-DELLHNVNAGK In a further embodiment the invention comprises synthesizing or obtaining the inhibitor and contacting said inhibitor with a sample comprising an alpha-helical coiled coil protein complex such as the 6HB and determining thereafter the ability of the inhibitor to bind to and/or inhibit the alpha-helical coiled coil protein complex activity characteristic for said viruses that use a class I fusion protein.

Also the inhibitor can be used for profiling or (cross-)resistance profiling and/or determining the binding affinity of said inhibitor for the alpha-helical coiled coil protein complex.

In another embodiment of the present invention the three-dimensional structure may be employed to design or select an inhibitor comprising computationally performing a fitting operation between the computer model of the 6HB and the computer model of the inhibitor, and evaluating the results of the fitting operation to determine the ability of the inhibitor to interact with the 6HB and/or to characterize the interaction of the inhibitor with the 6HB.

A crystal comprising the 6HB of RSV complexed with inhibitor, having the structural formula (I), having space group P2$_1$3 with unit cell edges of 63 Å±1 Å belongs to the invention as well.

Formulating the inhibitor as identified by the inventive method in a pharmaceutically acceptable form by, for instance, mixing the inhibitor or a derivative or homologue thereof with a pharmaceutically acceptable carrier is part of the invention as well.

Said inhibitor may be used to inhibit or prevent the membrane fusion process of viruses that use a class I fusion protein, such as RSV, with the cellular membrane of human cells.

Furthermore the invention relates to the use of an inhibitor, as identified by any of the methods according to the present invention, which binds the alpha-helical coiled coil protein complex of viruses that use a class I fusion protein, preferably RSV, in the manufacture of a medicament for treating respiratory tract infections.

The present invention further encompasses a similar method in accordance with the invention for identifying an inhibitor against other viruses that use a class I fusion protein. These viruses are listed in Tables 4 and 5 and show the aligned amino acids. The atomic coordinates of an alpha-helical coiled coil protein complex are used accordingly comprising those amino acids as aligned with the current HR1 and HR2 amino acids mentioned in Tables 4 and 5 hereunder.

TABLE 4

| | | | | | | |
|---|---|---|---|---|---|---|
| Paramyxovirus | RSV | S485 | D486 | E487 | F488 | D489 |
| Paramyxovirus | NDV | N460 | L461 | D462 | I463 | S464 |
| Paramyxovirus | SV5 | P446 | L447 | D448 | I449 | S450 |
| Paramyxovirus | HPIV1 | P456 | V457 | D458 | I459 | S460 |
| Paramyxovirus | HPIV2 | P450 | L451 | D452 | L453 | S454 |
| Paramyxovirus | HPIV3 | P453 | I454 | D455 | I456 | S457 |
| Paramyxovirus | Mumps | P447 | I448 | D449 | I450 | S451 |
| Paramyxovirus | Sendai | P460 | V461 | D462 | I463 | S464 |
| Paramyxovirus | Measles | R456 | L457 | D458 | V459 | G460 |
| Paramyxovirus | HMPV | E453 | D454 | Q455 | F456 | N457 |
| Paramyxovirus | Nipah | K453 | V454 | D455 | I456 | S457 |
| Paramyxovirus | Hendra | K453 | V454 | D455 | I456 | S457 |
| retrovirus | SIV | | | E114 | W115 | |
| retrovirus | HIV-1 | | | E630 | W631 | |
| retrovirus | Visna | | | Q777 | W778 | |

TABLE 5

| | | | | | | | | | |
|---|---|---|---|---|---|---|---|---|---|
| Paramyxovirus | RSV | D194 | L195 | K196 | N197 | Y198 | D200 | K201 | Q202 | L204 |
| Paramyxovirus | NDV | K181 | M182 | Q183 | Q184 | F185 | N187 | D188 | Q189 | N191 |
| Paramyxovirus | SV5 | A168 | V169 | Q170 | D171 | H172 | N174 | S175 | V176 | S178 |
| Paramyxovirus | HPIV1 | T177 | L178 | Q179 | D180 | F181 | N183 | N184 | E185 | R187 |
| Paramyxovirus | HPIV2 | A171 | I172 | Q173 | D174 | R175 | N177 | G178 | A179 | V181 |
| Paramyxovirus | HPIV3 | S174 | V175 | Q176 | D177 | Y178 | N180 | K181 | E182 | V184 |
| Paramyxovirus | Mumps | A167 | I168 | Q169 | D170 | H171 | N173 | T174 | I175 | N177 |
| Paramyxovirus | Sendai | T181 | L182 | Q183 | D184 | F185 | N187 | D188 | E189 | K191 |
| Paramyxovirus | Measles | G177 | V178 | Q179 | D180 | Y181 | N183 | N184 | E185 | I187 |
| Paramyxovirus | HMPV | E164 | L165 | K166 | D167 | F168 | S170 | K171 | N172 | T174 |
| Paramyxovirus | Nipah | A174 | L175 | Q176 | D177 | Y178 | N180 | T181 | N182 | V184 |
| Paramyxovirus | Hendra | A174 | L175 | Q176 | D177 | Y178 | N180 | T181 | N182 | V184 |
| retrovirus | SIV | W59 | G60 | T61 | K62 | N63 | Q65 | T66 | R67 | T69 |
| retrovirus | HIV-1 | W571 | G572 | I573 | K574 | Q575 | G577 | A578 | R579 | L581 |
| retrovirus | Visna | K718 | G719 | I720 | R721 | I722 | E724 | A725 | R726 | A728 |

Furthermore it is recognized by a skilled person that each amino acid type has its own conformers (=common rotamers).

In Table 1 of Simon C. Lovell, J. Michael Word, Jane S. Richardson, and David C. Richardson. "The Penultimate Rotamer Library", PROTEINS: Structure, Function, and Genetics. 40: 389-408 (2000) the possible rotamers are provided.

The binding pockets obtained by homology modeling based on FIG. 1 together with the sequence alignment in Tables 4 and 5 combined with the possible rotamers as given in Table 1 of the article of Lovell et al., mentioned above, are therefore also part of the invention.

The three-dimensional structure of the alpha-helical coiled coil protein complex of viruses that use class I fusion protein, is defined by a set of structure or atomic coordinates as set forth in FIG. 1. The term "structure or atomic coordinates" refers to Cartesian coordinates derived from mathematical equations related to the patterns obtained on diffraction of a monochromatic beam of X-rays by the atoms (scattering centers) of an alpha-helical coiled coil protein complex in crystal form. The diffraction data are used to calculate an electron density map of the repeating unit of the crystal. The electron density maps are then used to establish the positions of the individual atoms of the alpha-helical coiled coil protein complex.

For the purpose of this invention, any molecule or molecular complex that has a root mean square deviation of conserved residue backbones (N, C, CA, O) of less than 1.5 Å when superimposed on the relevant backbone atoms described by structure coordinates listed in FIG. 1 are considered identical.

The term "root mean square deviation" means the square root of the arithmetic mean of the squares of the deviations from the mean. It is a way to express the deviation or variation from a trend or object. For the purposes of this invention, the "root mean square deviation" defines the variation in the backbone of a protein or protein complex from the relevant portion of the backbone of the alpha-helical coiled coil protein complex as defined by the structure or atomic coordinates described herein.

The structure or atomic coordinates of the alpha-helical coiled coil protein complex and portions thereof are stored in a machine-readable storage medium. Such data may be used for a variety of purposes, such as drug discovery and x-ray crystallographic analysis of protein crystals.

BRIEF DESCRIPTION OF THE FIGURES

FIG. 1.

Figure 3:
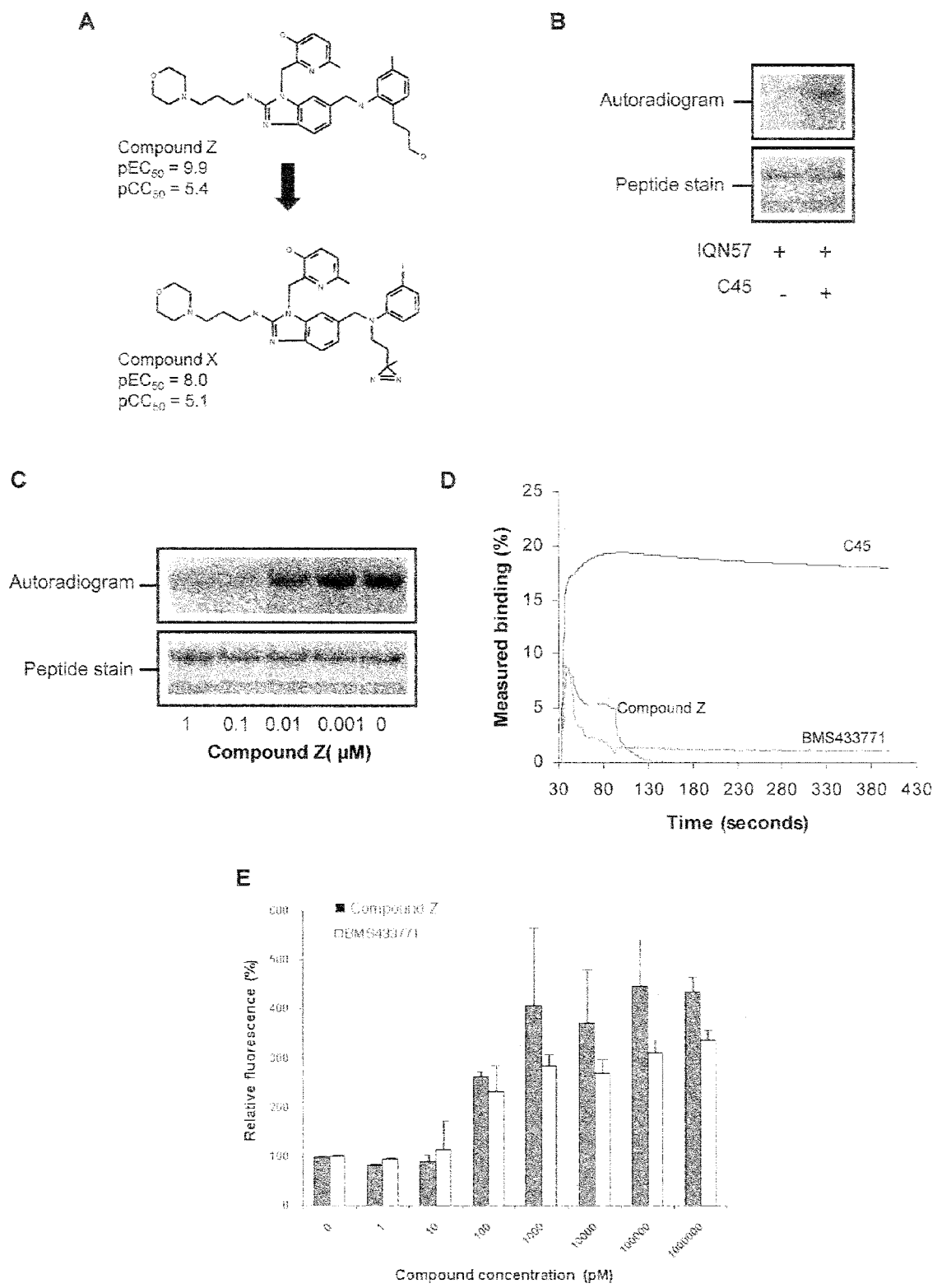

Atomic structure coordinates for the alpha-helical coiled coil protein in complex with Compound Z comprising among others the amino acids Tyr 198, Asp 200, Asp 486, Glu 487 and Phe 488 (referred to as 6HB) as derived by X-ray diffraction from crystals of that complex:

"Atom type" refers to the element whose coordinates have been determined.

Elements are defined by the first letter in the column.

"X,Y,Z" crystallographically define the atomic position determined for each atom.

"B" is a thermal factor that measures movement of the atom around its atomic center.

"Occ" is an occupancy factor that refers to the fraction of the molecules in which each atom occupies the position specified by the coordinates. A value of "1" indicates that each atom has the same conformation, i.e., the same position, in all molecules of the crystal.

FIG. 2.

Schematic view of compound Z positioned in the 6HB target site.

H-bonds are drawn as black dotted lines. Distances (Å) between interacting atoms are coloured black. Compound Z makes a π-π stacking interaction with Tyr 198. Amino acid residues from two neighbouring HR1 or HR1' and HR2 helices are indicated in green and blue, respectively. Compound Z is coloured by atom type (carbon=grey; oxygen=red; nitrogen=blue).

FIG. 3

A: structure of Compound Z and Compound X respectively
B: Binding assay results of compound X
C: competition assay results of compound Z
D: SPR analysis using C45, BMS433771 and compound Z
E: compound Z and BMS433771 facilitate the interaction of HR2 with the HR1-CTC

EXAMPLES

Example 1

Gene Construction, Purification, and Crystallization of RSV Fusion Peptides.

The N52 HR1 peptide was produced by expressing a 51 amino acid sequence corresponding to the proteinase K resistant core of the HR1 region of the hRSV F protein (Zhao et al. Proc Natl Acad Sci USA 97: 14172-14177, 2000) in Top10 *E. coli* (Invitrogen) as an N-terminal 6-histidine tagged Smt3 fusion protein (Mossessova et al. Mol Cell 5: 865-876, 2000) using the pBAD expression system (Invitrogen, Carlsbad, Calif., USA). Synthesized DNA was codon-optimised for expression in *E. coli*. The design allowed for a single alanine residue of the fusion construct to remain on the N-terminus after cleavage with Ulp1 protease, resulting in the 52 amino acid N52 peptide:

$AH^{159}$LEGEVNKIKSALLSTNKAVVSLSNGVSVLTSKV LDLKNYIDKQLLPIVN$K^{209}$ (SEQ ID NO:1).

Fermentation to express the Smt3-N52 fusion protein was done in 2×YT media in 9 liter batches in BIOSTAT fermentors (Sartorius BBI systems, Bethlehem, Pa., USA). Cells were lysed by sonication and the lysate clarified by ultracentrifugation. Initial purification was done in the denatured state. Guanidinium hydrochloride was added to the clarified lysate to a final concentration of 6.0 M before passage over a 15 mL HisTrap HP column (Amersham Biosciences, Piscataway, N.J., USA). The fusion protein was refolded on the column with a gradient from 6.0-0.0 M guanidinium hydrochloride over 5 column volumes in a running buffer of 100 mM Tris-HCl pH 8.0, 20 mM NaCl, 20 mM imidazole and eluted with a gradient from 20-500 mM imidazole over 12 column volumes. The fusion protein eluted at approximately 240 mM imidazole. The Smt3-N52 fusion protein was cleaved with Ulp1 protease at room temperature and final purification was achieved by RP-HPLC (Vydac C8, 22 mm×50 mm (19 mL), 5 mm particle size, 300 Å pore size (Grace Davison Discovery Sciences, Los Angeles, Calif., USA) using 0.1% trifluoroacetic acid (TFA) for the aqueous component of the mobile phase and 0.1% (v/v) TFA in acetonitrile for the organic component. N52 eluted at approximately 40% (v/v) acetonitrile and the 6xHis-Smt3 protein eluted at approximately 33% (v/v) acetonitrile. For physical analysis, the N52 peptide was lyophilised and re-suspended in 10 mM Tris-HCl pH 8.0/30 mM NaCl/0.04% (w/v) sodium azide. The final N52 peptide was highly pure and within 1.0 Da of the expected molecular mass as judged by SDS-PAGE and MALDI-ToF mass spectrometric analysis (PerSeptive Biosytems Voyager-DE STR, Applied Biosystems, Foster City, Calif., USA) operated in linear mode using sinapinic acid (SA) matrix. N52 eluted from the final RP-HPLC column was lyophilised and re-solubilised in 10 mM Tris-HCl pH 8.0/30 mM NaCl/0.04% (w/v) sodium azide to make an approximately 600 μM N52 sample.

The 39 amino acid C39 peptide with amino acid sequence $V^{482}$FPSDEFDASISQVNEKINQSLAFIRKSDELLHNVN AG$K^{520}$ (SEQ ID NO:2) was custom synthesized by Biopeptide (San Diego, Calif., USA) and delivered lyophilised and 98% pure after RP-HPLC.

The C-peptide used in the structure determination of hRSV fusion protein core, PDB accession code 1G2C, comprised 45 amino acids with the sequence NFYDPL$V^{482}$FPSDEFDA SISQVNEKINQSLAFIRKSDELLHNVNAG$K^{520}$ (SEQ ID NO: 3).—Compared with this C45 peptide, the C39 peptide was truncated at the N-terminus to obtain the proper length for C39 (Zhao et al. Proc Natl Acad Sci USA 97: 14172-14177, 2000).

The N52/C39 hexameric complex sample was prepared by adding the C39 peptide at a 1.1-fold molar excess to the N52 sample, and diluting with 10 mM Tris-HCl pH 8.0/30 mM NaCl/0.04% (w/v) sodium azide to make an approximately 500 μM (15 mg/ml peptide) N52/C39 sample. Compound Z was dissolved in DMSO to 100 mM and added to aliquots of the N52/C39 hexamer in a 3-fold molar excess over binding sites, giving a DMSO content of approximately 4.2%. The complex was incubated at room temperature for two days before crystallization trials were set up.

Crystallization of RSV N52/C39/Compound Z was performed at room temperature by sitting drop vapour diffusion. Equal volumes of N/C peptide hexamer complex crystallization sample and crystallization condition were combined to form the initial crystallization drop. Crystals of N52/C39/Compound Z were identified growing against the crystallization condition 30% (v/v) PEG-400/100 mM HEPES pH 7.5/200 mM NaCl. X-ray diffraction data were collected on an ADSC Quantum 210 CCD detector at the Advanced Light Source (ALS, Berkeley, Calif., USA) beamline 5.0.1 at a wavelength of 1.0 Å for N52/C39/Compound Z. The crystals were flash frozen in 80:20 crystallization condition:ethylene glycol, and data were collected on the frozen crystals at 100 K. All X-ray diffraction data were reduced with HKL2000 (Otwinowski et al. In Methods in Enzymology 276: Macromolecular Crystallography, part A (eds. Carter, C. W., Jr. & Sweet, R. M.) 307-326 (New York, 1997)). Reduced intensity data were converted to structure factors with TRUNCATE (French et al. Acta Crystallogr A 34: 517-525, 1978).

The X-ray diffraction data were scaled in space group $P2_13$ for N52/C39/Compound Z.

The structure of N52/C39/Compound Z was determined by molecular replacement with MOLREP (Vagin et al. Appl Cryst 30: 1022-1025, 1997) using the data from 20.0-3.0 Å resolution. The search model was derived from RCSB protein data bank deposition 1G2C (chain A-HR1 residues 160-204, chain B-HR2 residues 480-514). The initial molecular replacement model was refined with REFMAC (Murshudov et al. Acta Crystallogr D Biol Crystallogr 53: 240-255, 1997) using data from 20.0-2.1 Å resolution to an $R_{factor}$ of 0.272 ($R_{free}$ 0.284) after which difference electron density corresponding to bound Compound Z was clearly apparent in σA-weighted (Read. Acta Crystallogr A 42: 140-149, 1986) $F_{obs}$-$F_{calc}$ electron density maps. Compound Z was modelled using the CCP4i Monomer Library Sketcher (Potterton et al. Acta Crystallogr D Biol Crystallogr 59: 1131-1137, 2003) and fitted to the electron density maps with COOT (Emsley et al. Acta Crystallogr D Biol Crystallogr 60: 2126-2132, 2004).

The X-ray structure analysis (interactions, ψ-angle, χ1-angle) was performed with Sybyl 7.2 software on a Linux workstation and the figures were created with Benchware 3D Explorer on a Windows workstation (Tripos Associates Inc., St. Louis, Mo., USA).

TABLE 1

Data collection and refinement statistics

| | |
|---|---|
| Xray Source | ALS 5.0.1 |
| Date | Jul. 02, 2003 |
| Crystal: | Ndel/C39/CmpdZ |
| Space_Group | P213 P213 |
| Patterson_Symmetry | CUBIC_2/m_-3 CUBIC_2/m_-3 |
| Unit_Cell (Å) | 63.2 |
| Model_Contents | Ndel: 159-207, |
| Protein | C: 483-517 |
| Waters | 37 |
| HET_groups | Compound Z, PEG200 |
| Data_Collection: | |
| Resolution (Å) | 44.72-1.47 |
| High_res_shell (Å) | 1.510-1.470 |
| Completeness (%) | 100 |
| High_res_shell (%) | 100 |
| observations | 146360 |
| reflections | 14612 |
| Multiplicity | 10 |
| Wilson_B (Å$^2$) | 18.1 |
| R-merge | 0.071 |
| High_res_shell | 0.692 |
| Refinement: | |
| Resolution (Å) | 20.00-1.47 |
| High_res_shell (Å) | 1.49-1.47 |
| r.m.s._deviations_of_the_model | |
| bonds (Å) | 0.015 |
| angles (°) | 1.736 |
| planarity (Å) | 0.007 |
| vdw (Å) | 0.24 |
| esu_by_ML (Å) | 0.04 |
| R-factor(work) | 0.163 |
| High_res_shell | 0.19 |
| R-factor(free) | 0.196 |
| High_res_shell | 0.21 |

It has thus been shown by virological and biochemical studies that a small molecule with structural formula (I), also called inhibitor or compound Z, with very potent activity against hRSV, works as a fusion inhibitor by interfering with the 6HB-formation. A high-resolution crystal structure of the complex "Compound Z/6HB" (1.47 Å resolution) was formed. Thereto, a 52 (N52) and a 39 (C39) amino acid residue peptide, corresponding to the proteinase K resistant core of the HR1 and HR2 domain of the fusion protein respectively, were co-crystallized with compound Z. The space group is P2$_1$3 with unit cell edges of 63 Å±1 Å. The asymmetric unit contains the inhibitor surprisingly complexed to the heterodimer of one N52 and one C39 peptide. The complete 6HB is generated by the three-fold rotation axis along the diagonal of the cubic unit cell. Compound Z was fitted unambiguously into the electron density maps. Compound Z makes several hydrophobic and electrostatic interactions with HR1 amino acid residues of the highly conserved hydrophobic pocket. The side chain of asp 200 forms a hydrogen bond with the hydroxyl-group from the hydroxypyridine moiety. Compared with its orientation in the 1G2C crystal structure from the 6HB of RSV, the side chain from the Asp 200 is turned to the inside of the complex due to its interactions with compound Z. In addition, the hydroxylpyridine moiety from compound Z forms a parallel pi-pi stacking with the side-chain from tyr 198 and a parallel pi-pi stacking with the side chain of phe 488. A second, perpendicular pi-pi stacking interaction is formed between the Tyr 198 side chain and the benzimidazole scaffold from compound Z. The hydroxylpyridine is sandwiched between Tyr 198 and Phe 488, but does not displace Phe 488 when compared to the 1G2C structure. The other substituents of the benzimidazole scaffold, the substituted phenyl ring and the morpholino ring, are in contact with the surface of the HR1 trimer and make van der Waals non polar/polar interactions. From the refinement solution, it appeared that compound Z is sandwiched between the N52 and the C39 peptides. In addition to several interactions with HR1, compound Z also makes several important interactions with conserved HR2 amino acid residues. The nitrogen atom substituting directly the benzimidazole moiety from compound Z makes a hydrogen bond with the Asp 486. The hydroxypyridine also forms a parallel pi-pi stacking with Phe 488. Additionally, a water-facilitated hydrogen-bonding network between the side chain of Glu 487 and both the hydroxyl-group from the propanol chain of compound Z and the hydroxypyridine is formed. Finally, an internal hydrogen bond between the hydroxyl-group from the propanol chain and the amino-group next to the aniline moiety is formed. The presented co-crystal structure allows the dissection of structural features responsible for the binding of compound Z with its 6HB target.

The 6HB is an interesting drug target because the genetic barrier for raising viral resistance against a compound interfering with HR1-HR2 binding is likely increased, due to the high sequence conservation observed for HR1 and HR2 (Collins et al. In Fields Virology, 4th Edition (eds. Howley, P. M. et al.) 1443-1485 Philadelphia, 2001)). Nevertheless, two mutations, Asp 486 to Asn (HR2) and Ser 398 to Leu (loop region between HR1 and HR2 domains), selected for a Compound Z-resistant viral phenotype by serial passaging of hRSV in HeLa cells in the presence of increasing concentrations of compound. The Asp 486 to Asn mutation can be explained by the observed binding mode of the compound, as the sidechain of Asp 486 is involved in both inter- and intramolecular hydrogen bonds. The Asp 486 to Asn mutation is likely to preclude compound binding by disrupting the conformation of that region of the binding site and/or destabilizing the intermolecular hydrogen bond with Compound Z. Since the exact function of the loop region has not been elucidated, it is less clear why the Ser 398 to Leu loop mutation selects for resistance against Compound Z. Binding of the compound to the nascent 6HB could affect the kinetics of 6HB formation during viral fusion (Russell et al. J Cell Biol 163: 363-374, 2003), and mutations in this loop region could be aimed at re-establishing the correct timing of 6HB formation (Russell et al. J Cell Biol 163: 363-374, 2003; Douglas et al. Antimicrob Agents Chemother 49: 2460-2466, 2005).

The crystal structure presented here has considerably improved our docking models as compared to earlier binding models based on the published unliganded 6HB structure (Zhao et al. Proc Natl Acad Sci USA 97: 14172-14177, 2000), since it represents a binding mode which is fully consistent with the structure-activity relationship (SAR) observed for the Compound Z (compound 1 in Table 2) series of inhibitors. Removal of the hydroxypropyl group caused a 1.3 log reduction in activity (compound 2), and further truncation of the methylamino-toluene moiety yielded a further 0.8 log decrease in potency (compound 3). These dramatic effects are likely due to unfavourable changes in the observed water-mediated hydrogen bonding network and an overall reduction in hydrophobic binding contacts. The morpholinopropyl group is observed to slightly decrease the activity, as its removal gave a 0.6 log improvement in activity (compound 4). However, we note that this group was incorporated for its provision of a better pharmacokinetic profile (Bonfanti et al. J Med Chem 50: 4572-4584, 2007). The amino substituent at position 2 of the benzimidazole is key. Removal of this one atom (compound 5) led to a 2.6 log reduction in activity, highlighting the extreme importance of the interaction with Asp 486. The importance of this binding contact was further established by a dramatic 3.4 log reduction in antiviral activity observed for Compound Z against a virus bearing the Asp 486 to Asn resistance-associated mutation. Finally, the observed interaction between the pyridine hydroxyl and Asp 200 is consistent with the 1.3 log drop in activity observed for the methoxy analogue (compound 6).

Table 2: Compound Z (=Compound 1 Below) and Analogues.

Structures of compound 1 and analogues are shown together with their activity in an RSV antiviral cellular assay. In vitro activity is reported as $pEC_{50}$ [$-\log_{10} EC_{50}$ (M)].

TABLE 2

| compound Z and analogs | | |
|---|---|---|
| Compound | Structure | In vitro activity ($pEC_{50}$) |
| 1 | 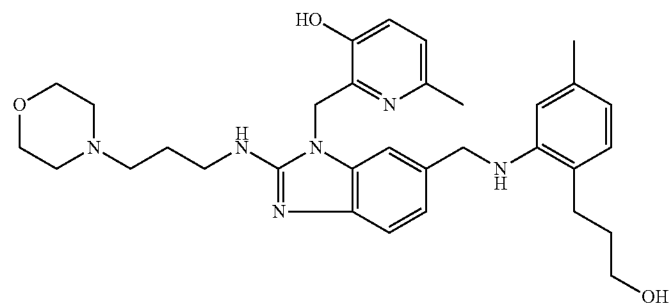 [SMILES: Cc1ccc(CCCO)c(NCc2ccc3nc(NCCCN4CCOCC4)n(Cc4nc(C)ccc4O)c3c2)c1]  | 9.9 |
| 2 | 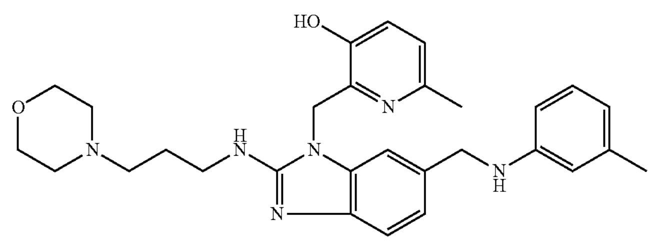 [SMILES: Cc1cccc(NCc2ccc3nc(NCCCN4CCOCC4)n(Cc4nc(C)ccc4O)c3c2)c1]  | 8.6 |
| 3 | 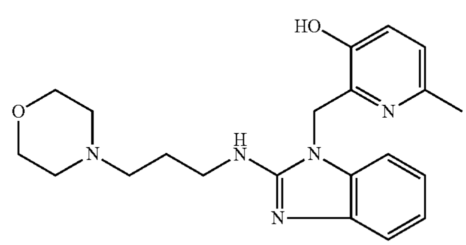 [SMILES: Cc1ccc(O)c(Cn2c(NCCCN3CCOCC3)nc3ccccc32)n1]  | 6.8 |
| 4 | 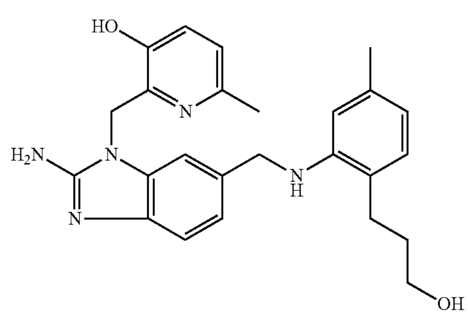 [SMILES: Cc1ccc(CCCO)c(NCc2ccc3nc(N)n(Cc4nc(C)ccc4O)c3c2)c1]  | 10.5 |

TABLE 2-continued compound Z and analogs

| Compound | Structure | In vitro activity (pEC$_{50}$) |
|---|---|---|
| 5 | [structure] | 7.9 |
| 6 | [structure] | 8.6 |

Compound Z Binding Mode:

The interactions of compound Z with the fusion peptide (protein) are shown in the FIG. 2 (Interaction map of Compound Z with its 6HB target site). The compound Z binds the 6-helix bundle part of the F protein and is sandwiched between N52 and C39. This inhibitor interferes with the interaction of key amino acid (residue Phe 488) from the HR2 with the prominent cavity in the groove formed by two neighbouring HR1 helices that are part of the central trimeric coiled-coil protein complex and that this interference abrogates fusion.

Hydrophobic Interactions:

Tyr 198 (HR1) and Phe 488 (HR2), which form a part of the P1 pocket, are in contact with the hydroxylpyridine part of compound Z. The benzimidazole scaffold is also in contact with Tyr 198. These two aromatic systems interact with Tyr 198 forming a double pi-stacking interaction (parallel and perpendicular). The hydroxylpyridine is sandwiched between Tyr 198 and Phe 488 but does not displace Phe 488.

The other substituents of the benzimidazole scaffold, the substituted phenyl ring and the morpholino ring, are in contact with the surface of the HR1 trimer and make van der Waals non polar/polar interactions.

Main Hydrogen Bonds:

The hydroxyl (pyridine) moiety makes a direct specific hydrogen bond with Asp 200 (HR1). This aspartic acid was oriented out of the P1 pocket in the so-called 1G2C structure (Zhao et al. Proc Natl Acad Sci USA 97: 14172-14177, 2000). The nitrogen atom substituting directly the benzimidazole is hydrogen bonded to Asp 486.

The additional hydrogen-bonding network observed in this structure is summarized in Table 3: a hydrogen bond is mediated by a water molecule from the hydroxyl (propanol) and pyridine of compound Z to the side chain of Glu 487.

TABLE 3

| Hydrogen bond interactions between compound Z, fusion peptide and structured water molecule. Hydrogen bond interactions | | | | |
|---|---|---|---|---|
| Inhibitor Atom | Protein Atom | Inhibitor Atom | Water Atom | Distance (Å) |
| N(H) (benzimidazole substitution) | O (Asp 486) | | O(H) | 2.87 |
| N (hydroxylpyridine) | | | | 2.84 |
| N(H) (phenyl ring substitution) | | O(H) (propanol) | | 2.90 |
| O(H) (hydroxylpyridine) | O (Asp 200) | | | 2.58 |
| O(H) (propanol) | | | O | 2.74 |
| | O (Glu 487) | | O(H) | 2.75 |

Structural features responsible for the binding of compound Z to the 6-HB were demonstrated. The remarkable feature of the interaction between compound Z and the fusion protein is the network of four hydrogen-bonding interactions: two of them are direct with the protein, whereas two others are mediated by a water molecule. The interesting interaction is the double pi-stacking between the pyridine/benzimidazole of compound Z and Tyr 198.

Mutation at Asp 486 to Gln however causes loss of the key interaction of the aspartic acid to an amino group of compound Z. As a result a mutation at this position then directly affects interaction with the inhibitor or compound Z.

The observed binding mode establishes a novel induced fit mechanism in which the displaced HR2 residues reorient themselves and contribute to the observed inhibitor binding site indicating that in addition to the interaction with the groove of two neighbouring HR1 helices of the 6HB, one needs interactions with HR2 amino acid residues in order to obtain optimal 6HB fusion inhibitors.

Example 2

Compound Z, compound X (both structural formulas provided in FIG. 3A) and BMS433771 were synthesized according to described methods (Bonfanti et al., J. Med. Chem. 51, 875-896 (2008). The chemical structure of BMS433771 as such is disclosed in Cianci et al., PNAS, 101, 15046-15051 (2004) more specifically on page 15048 (FIG. 1) and is herewith incorporated by reference for this structure. Peptides were custom synthesized at Abgent (San Diego, Calif., USA) and delivered lyophilized and 98% pure after RP-HPLC.

Photo Affinity Labeling of hRSV and Synthetic $F_1$ Peptides

Affinity labeling of synthetic $F_1$-derived peptides was performed by mixing 25 μM concentrations of peptide in binding buffer (PBS+5% DMSO+10% glycerol+an additional 100 mM NaCl) with 10 nM [$^{125}$I] Compound x (50 nM stock, 2000 Ci/mmol in methanol). Samples were irradiated for 15 min with long wave UV light. Samples were resuspended in 20 μL of a mix of LDS NuPage loading buffer (Invitrogen, Merelbeke, Belgium) and reducing agent (Invitrogen) and heated for 20 min at 72° C. Samples were run under reducing conditions on a NuPage 4-12% Bis-Tris polyacrylamide gel (Invitrogen). Before the gels were dried and autoradiographed, the peptides were visualized by Coomassie staining.

SPR Biosensor Analysis

20 μM biotinylated-IQN57 was immobilized on a Streptavidin-certified sensor chip (GE Healthcare, Diegem, Belgium) surface in PBS at a flow rate of 10 μl/min and a contact time of 7 min. A reference flow cell was used as a control for nonspecific binding and refractive index changes. 30 μM Compound Z, 30 μM BMS433771 or 10 μM C45 peptide concentrations were injected for 60 seconds at a flow rate of 90 μl/min and the dissociation was followed for 5 min. Several PBS+5% dimethylsulfoxide (DMSO; Sigma Aldrich NV, Bornem, Belgium) buffer blanks were injected over the course of an experiment for double referencing. The flow system was washed between sample injections with running buffer containing 50% DMSO, and the immobilized surface was regenerated with one injection of 0.2% sodiumdodecylsulfate for 30 sec. SPR biosensor data were collected on a BIAcore S51. All experiments were conducted at 20° C. Binding results were presented as the percentage of the fraction of a compound or peptide that was measured to be bound to IQN57 when compared to the maximal binding (Rmax) theoretically possible for this compound or peptide, under the same experimental conditions.

6HB-formation ELISA

White streptavidin-coated 96-well plates (NoAb Biodiscoveries, Mississauga, Canada) were blocked with PBS+5% BSA for 1 h and then washed three times with PBS. 10 nM biotin-labeled IQN57 dissolved in PBS+1% BSA was noncovalently bound to the surfaces of the 96-well plate for 30 min and then wells were washed again 3 times with PBS. Different concentrations of compound Z or BMS433771 were mixed together with 10 pM FITC-labeled C45 in PBS+ 0.5% DMSO+1% BSA, added to the wells and incubated for 30 min, and then washed three times with PBS. Subsequently, POD-conjugated anti-FITC Fab fragment (1:5000) (Roche Applied Science, Vilvoorde, Belgium) in PBS+1% BSA was administered to the wells and incubated for 30 min. Finally, wells were washed again three times with PBS, Supersignal West Femto chemiluminescent substrate from Pierce (Perbio Science, Erembodegem, Belgium) added and signals were analyzed on a ViewLux UltraHTS microplate reader (Perkin Elmer, Zaventem, Belgium). Assay conditions without addition of biotin-labeled IQN57, FITC-labeled C45, POD-conjugated anti-FITC Fab fragment, or chemiluminescent substrate were included as negative controls or control of background signal in each of the experiments. In addition, assay conditions with saquinavir, Fuzeon® (T20), or the HIV-1-derived HR1 peptide (biotin-labeled IQN36) were used as specificity controls in each experiment.

Results

To allow the deposition of their nucleic acid genome into a host cell, and to initiate their replication cycle, enveloped viruses have evolved a complex membrane fusion machinery that includes a fusion protein (F protein). Based on structural similarities, the F proteins from different viruses have been grouped into three distinct classes: class I, II and III. Some prototypic members of the trimeric class I fusion proteins include HIV-1 gp41, influenza hemagglutinin and the F proteins from paramyxoviruses.

After initiation of fusion, the fusion protein of viruses using class I fusion proteins undergoes dramatical refolding. A folding intermediate of the fusion protein is formed that contains a HR1 central trimeric coiled-coil (HR1-CTC). In the final stages of refolding of the fusion protein, the HR1-CTC forms together with three HR2 alpha helices a six-helix bundle (6HB) that brings the viral and cellular membranes into close proximity with each other, and enables them to merge. The formation of the 6HB is crucial to complete the viral fusion process.

Many of the small molecules that inhibit the fusion process of viruses using a class I fusion protein are currently believed to inhibit this process by binding into a hydrophobic pocket that is present in each of the grooves of the HR1-CTC of the fusion protein. It is assumed that the small molecules prevent the formation of a six-helix bundle (6HB) by binding to the HR1 hydrophobic pocket and to sterically compete with HR2 amino acids that naturally occupy the hydrophobic pocket upon formation of the 6HB.

The current assumption in the prior art about the mechanism of action of these fusion inhibitors is insufficient.

First, our data demonstrated that binding of Compound Z is dependent not only on interacting with HR1 but unexpectedly also with HR2 (FIG. 2). This is shown by using compound X, an active close analog of compound Z containing a diazirine moiety and an iodine atom (FIG. 3A). The diazirine moiety allows the compound to be covalently coupled to its target site by irradiating it with long wave UV light. The iodine atom was introduced to allow radio labeling of compound X with $^{125}$I. Binding of compound X was only observed when peptides representing both HR1 (IQN57) and HR2 (C45) heptadrepeats were present in the binding assay FIG. 3B). Only if a HR1 peptide was present in the assay, no binding was observed. It was also demonstrated that compound Z and compound X competed for the same binding pocket (FIG. 3C). These results clearly demonstrate that interactions with HR2 are required for compound Z binding. Hence, its binding pocket is constituted of amino acids from both HR1 and HR2 heptad repeats and not only with amino acids from HR1 alone as assumed in the prior art.

Second, it has been published in the prior art that BMS433771 binds to the HR1 hydrophobic pocket (Cianci et al., PNAS, 101, 15046-15051, 2004). Nevertheless, some questions remain whether binding of this compound to the HR1 hydrophobic pocket explains the potent antiviral activity of the compound, since it was shown that binding of this compound to an HR1-derived peptide alone was relatively weak.

Our data further highlight this by demonstrating using SPR analysis that both compound Z and BMS433771 do not bind to the HR1 hydrophobic pocket alone (FIG. 3D). Moreover, this compound was also demonstrated to bind to the F protein of hRSV in its prefusogenic conformation. Based on recent structural insights from the prefusion structure of the SV5 fusion protein however, the HR1 hydrophobic pocket is not present in the prefusogenic state of the fusion protein.

Third, we show that both compounds (compound Z and BMS433771) facilitate the interaction of HR2 with the HR1-CTC (FIG. 3E), indicating that the compounds inhibit fusion by inducing 6HB formation prematurely instead of preventing 6HB formation by sterically hindering the association of HR2 with the HR1-CTC, as currently described in the prior art.

Finally, several observations currently present in the prior art further indicate that interactions with both HR1 and HR2 are required for binding and antiviral activity of small molecules that target this region of the 6HB. Small molecule HIV-1 6HB inhibitors all suffer from limited potency. They only seem to have interactions with the HR1 heptad-repeat, and compete with the HR2 amino acids that naturally occupy the HR1 hydrophobic pocket, thereby completely preventing the HR2 interactions with the HR1-CTC. Small molecule organic building blocks that were coupled covalently to a peptide derived from the HR2 sequence of HIV-1, demonstrated high nanomolar activity. However, the organic building blocks interacting with the HR1 hydrophobic pocket, improved the activity of the peptide about 20-fold when coupled to the peptide, but did not display any activity on their own. Hence, interactions with both HR1 and HR2 may be a more general requirement for small molecules targeting the 6HB.

The invention claimed is:

1. A method for identifying an inhibitor against viruses that use a class I fusion protein comprising the steps of
using the atomic coordinates of an alpha-helical coiled coil protein complex comprising amino acids Asp 194, Leu 195, Lys 196, Asn 197, Tyr 198, Asp 200, Lys 201, Gln 202, Leu 204, Ser 485, Asp 486, Glu 487, Phe 488, and Asp 489 according to FIG. 1±a root mean square deviation from the backbone atoms of said amino acids of not more than 1.5 Angstrom to generate a three-dimensional structure of a molecule comprising an alpha-helical coiled coil protein complex binding pocket wherein said alpha-helical coiled coil protein complex binding pocket is a six-helix bundle (6HB);
employing said three-dimensional structure to design or select said inhibitor wherein employing said three-dimensional structure to design or select an inhibitor comprises computationally performing a fitting operation between the computer model of the 6HB and the computer model of the inhibitor, and evaluating the results of the fitting operation to determine the ability of the inhibitor to interact with the 6HB and/or to characterize the interaction of the inhibitor with the 6HB; and
contacting said inhibitor with a sample comprising an alpha-helical coiled coil protein complex and determining thereafter the ability of said inhibitor to bind to and inhibit an alpha-helical coiled coil protein complex activity characteristic for said viruses that use a class I fusion protein.

2. A method for identifying an inhibitor against viruses that use a class I fusion protein comprising the steps of
using the atomic coordinates of an alpha-helical coiled coil protein complex comprising amino acids Tyr-198, Asp-200, Asp-486, Glu-487 and Phe-488 according to FIG. 1±a root mean square deviation from the backbone atoms of said amino acids of not more than 1.5 Å, to generate a three-dimensional structure of a molecule comprising an alpha-helical coiled coil protein complex binding pocket wherein said alpha-helical coiled coil protein complex binding pocket is a six-helix bundle (6HB);
employing said three-dimensional structure to design or select said inhibitor wherein employing said three-dimensional structure to design or select an inhibitor comprises computationally performing a fitting operation between the computer model of the 6HB and the computer model of the inhibitor, and evaluating the results of the fitting operation to determine the ability of the inhibitor to interact with the 6HB and/or to characterize the interaction of the inhibitor with the 6HB; and
contacting said inhibitor with a sample comprising an alpha-helical coiled coil protein complex and determining thereafter the ability of said inhibitor to bind to and/or inhibit an alpha-helical coiled coil protein complex activity characteristic for said viruses that use a class I fusion protein.

3. The method according to claim 1 wherein said alpha-helical coiled coil protein complex is a six-helix bundle (6HB) characteristic for said viruses that use a class I fusion protein and wherein said inhibitor has the following interactions with heptad-region 1 (HR1) of said 6HB:
a hydrogen bond between a hydroxypyridine moiety of said inhibitor and the side chain of Asp 200 of said HR1;
a parallel pi-pi stacking between the hydroxypyridine moiety of said inhibitor and the side chain of Tyr 198 of said HR1;
a perpendicular pi-pi stacking between a benzimidazole group of said inhibitor and the side chain of Tyr 198 of said HR1 and
hydrophobic interactions between the aniline moiety of said inhibitor and HR1.

4. The method according to claim 1 further comprising the following interactions between heptad-region 2 (HR2) of said 6HB and said inhibitor:
a hydrogen bond between an amino-group, located between a propylmorpholino moiety and a benzimidazole ring of said inhibitor, and the side chain of Asp 486 of said HR2;
a structured water mediated hydrogen bonding network formed between the side chain of Glu 487 of said HR2 and a propanol hydroxyl and a hydroxypyridine nitrogen of said inhibitor and
a parallel pi-pi stacking between the benzimidazole ring of said inhibitor and the side chain of Phe 488 of said HR2.

5. The method of claim 1 further comprising subjecting the inhibitor to profiling or (cross-) resistance profiling.

6. The method of claim 1 further comprising determining the binding affinity of the inhibitor for the alpha-helical coiled coil protein complex.

7. The method according to claim 1 further comprising formulating the inhibitor identified in a pharmaceutically acceptable form.

8. A method for the production of a pharmaceutical composition comprising the method of claim 1 and furthermore mixing the inhibitor identified or a derivative or homologue thereof with a pharmaceutically acceptable carrier.

* * * * *

```
                          SEQUENCE LISTING

<160> NUMBER OF SEQ ID NOS: 3

<210> SEQ ID NO 1
<211> LENGTH: 52
<212> TYPE: PRT
<213> ORGANISM: respiratory syncytial virus

<400> SEQUENCE: 1

Ala His Leu Glu Gly Glu Val Asn Lys Ile Lys Ser Ala Leu Leu Ser
1               5                   10                  15

Thr Asn Lys Ala Val Val Ser Leu Ser Asn Gly Val Ser Val Leu Thr
            20                  25                  30

Ser Lys Val Leu Asp Leu Lys Asn Tyr Ile Asp Lys Gln Leu Leu Pro
        35                  40                  45

Ile Val Asn Lys
    50

<210> SEQ ID NO 2
<211> LENGTH: 39
<212> TYPE: PRT
<213> ORGANISM: respiratory syncytial virus

<400> SEQUENCE: 2

Val Phe Pro Ser Asp Glu Phe Asp Ala Ser Ile Ser Gln Val Asn Glu
1               5                   10                  15

Lys Ile Asn Gln Ser Leu Ala Phe Ile Arg Lys Ser Asp Glu Leu Leu
            20                  25                  30

His Asn Val Asn Ala Gly Lys
        35

<210> SEQ ID NO 3
<211> LENGTH: 45
<212> TYPE: PRT
<213> ORGANISM: respiratory syncytial virus

<400> SEQUENCE: 3

Asn Phe Tyr Asp Pro Leu Val Phe Pro Ser Asp Glu Phe Asp Ala Ser
1               5                   10                  15

Ile Ser Gln Val Asn Glu Lys Ile Asn Gln Ser Leu Ala Phe Ile Arg
            20                  25                  30

Lys Ser Asp Glu Leu Leu His Asn Val Asn Ala Gly Lys
        35                  40                  45
```